(12) United States Patent
Trager et al.

(10) Patent No.: US 11,970,743 B2
(45) Date of Patent: Apr. 30, 2024

(54) GENE EXPRESSION MARKERS FOR PREDICTING OVERALL SURVIVAL IN SUBJECTS TREATED WITH SIPULEUCEL-T

(71) Applicant: Dendreon Pharmaceuticals LLC, Seal Beach, CA (US)

(72) Inventors: James B. Trager, Seattle, WA (US); Nadeem A. Sheikh, Seattle, WA (US); Debraj GuhaThakurta, Bellevue, WA (US); Harini Kandadi, East Windsor, NJ (US); Li-Qun Fan, Bellevue, WA (US)

(73) Assignee: Dendreon Pharmaceuticals LLC, Seal Beach, CA (US)

( * ) Notice: Subject to any disclaimer, the term of this patent is extended or adjusted under 35 U.S.C. 154(b) by 452 days.

(21) Appl. No.: 16/565,185

(22) Filed: Sep. 9, 2019

(65) Prior Publication Data
US 2020/0017921 A1    Jan. 16, 2020

Related U.S. Application Data

(63) Continuation of application No. 15/268,267, filed on Sep. 16, 2016, now abandoned.

(60) Provisional application No. 62/242,113, filed on Oct. 15, 2015.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,976,546 A | 11/1999 | Laus et al. |
| 6,080,409 A | 6/2000 | Laus et al. |
| 6,210,662 B1 | 4/2001 | Laus et al. |
| 7,413,869 B2 | 8/2008 | Law et al. |
| 8,843,320 B2 | 9/2014 | Shaughnessy et al. |
| 2005/0244966 A1 | 11/2005 | Efrat |
| 2010/0304988 A1 | 12/2010 | Brouard et al. |
| 2014/0302060 A1 | 10/2014 | Beg et al. |
| 2014/0377220 A1 | 12/2014 | Bismar |
| 2015/0044224 A1 | 2/2015 | Soliman et al. |
| 2017/0107580 A1* | 4/2017 | Trager ................ C12Q 1/6886 |

FOREIGN PATENT DOCUMENTS

| | | |
|---|---|---|
| EP | 2 885 428 A1 | 6/2015 |
| WO | 2012/015765 A2 | 2/2012 |
| WO | 2013/060739 A1 | 5/2013 |
| WO | 2013/149039 A1 | 10/2013 |
| WO | 2014/028925 A1 | 2/2014 |

OTHER PUBLICATIONS

Oh et al. (J. Clinical Oncology May 20, 2016 34(15-supplement): 5026), (Year: 2016).*
Kantoff et al. (New Engl. J. Med. Jul. 29, 2010 363(5): 411-22 (Year: 2010).*
Alter et al. (2000) "Singular value decomposition for genome-wide expression data processing and modeling," Proc Natl Acad Sci USA 97(18): 10101-10106.
Halabi e al. (2003) "Prognostic model for predicting survival in men with hormone-refractory metastatic prostate 15 cancer," J Clin Oncol 21(7): 1232-1237.
Halabi et al. (2014) "Updated prognostic model for predicting overall survival in first-line chemotherapy for patients with metastatic castration-resistant prostate cancer," J Clin Oncol 32(7): 671-677.
Harm et al. (2014) "Immunotherapy for prostate cancer: lessions from responses to tumor-associated antigens," Front Immunol. 5(191): 15 pages.
"Qiagen Digital Insights" available at www.ingenuity.com/products/pathways_analysis.html, 2 pages, Dec. 2022.
Klatte et al. (2009) "Signal Transduction," Chapter 4 in Pfannschmidt (Ed.), Humana Press: 61-77.
Mecham et al. (2010) "Supervised normalization of microarrays," Bioinformatics 26(10): 1308-1315.
NanoString Technologies, Inc. (2011) "nCounter Expression Data Analysis Guide," User Guide: 1-20.
Olmos et al. (2012) "Prognostic value of blood mRNA expression signatures in castration-resistant prostate cancer: a prospective, two-stage study," The Lancent Oncology 13(11): 1114-1124.
Bio-Rad Laboratories, Inc. (2014) "PrimePCR Assays and Panels," Interactive PDF, 20 pages.
Ross et al. (2012) "A whole-blood RNA transcript-based prognostic model in men with castration-resistant prostate cancer: a prospective study," The Lancet Oncology 13(11): 1105-1113.
Sheikh et al. (2013) "Sipuleucel-T immune parameters correlate with survival: an analysis of the randomized phase 3 clinical trials in men with castration-resistant prostate cancer," Cancer Immunol Immunother 62:137-147.
Jemal et al. (2009) "Cancer Statistics," CA Cander J Clin 59(4): 225-249.

(Continued)

*Primary Examiner* — Peter J Reddig
(74) *Attorney, Agent, or Firm* — Jodi A. Reynolds, Esq.; Harter Secrest & Emery LLP

(57) ABSTRACT

Gene expression profiling in patients with mCRPC identifying genes that predict overall survival in response to treatment with sipuleucel-T, the method comprising the steps of (a) determining a gene expression level of a first biomarker; (b) determining a gene expression level of at least one additional biomarker different from the first biomarker; and (c) transforming the expression level of the first biomarker and the at least one additional biomarker into a first score corresponding to a probability of overall survival in response to treatment with sipuleucel-T.

16 Claims, 5 Drawing Sheets

(56) References Cited

OTHER PUBLICATIONS

Figure 1:
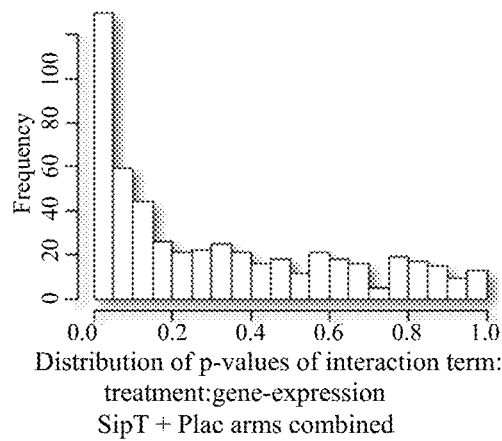
Figure 1:
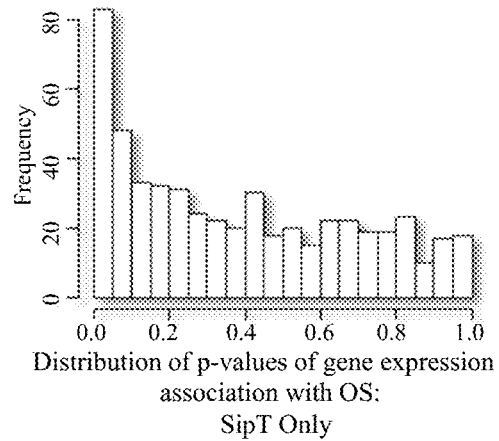

Tibshirani (1996) "Regression Shrinkage and Selection via the Lasso," Journal of the Royal Statistical Society (Series B)58: 267-288.

Zou et al. (2003) "Regularization and Variable Selection via the Elastic Net," Journal of the Royal Statistical Society: Series B (Statistical Methodology) 67(2): 301-320.

"GeneCards: The Human Gene Database" available at www.genecards.org/, 1 page, Nov. 9, 2022.

* cited by examiner

GENE EXPRESSION MARKERS FOR PREDICTING OVERALL SURVIVAL IN SUBJECTS TREATED WITH SIPULEUCEL-T

RELATED APPLICATIONS

This application is a continuation of U.S. patent application Ser. No. 15/268,267, filed Sep. 16, 2016, and claims the benefit of priority to U.S. Provisional Patent Application Ser. No. 62/242,113, filed on Oct. 15, 2015, the content of which provisional application is relied upon and incorporated herein by reference in its entirety.

STATEMENT REGARDING FEDERALLY SPONSORED RESEARCH OR DEVELOPMENT

None.

BACKGROUND OF THE INVENTION

Field of the Invention

The present invention relates generally to the field of prostate cancer research and in particular to predictive biomarkers useful in prognosis or predicting overall survival (OS) in a subject with metastatic castration-resistant prostate cancer (mCRPC) after treatment with sipuleucel-T.

Description of Related Art

In the United States, prostate cancer is the most common noncutaneous cancer and the second leading cause of cancer death in men (Jemal A, Siegel R, Ward E, Hao Y, Xu J, Thun M J. Cancer statistics, 2009. CA Cancer J Clin 2009; 59:225-49). Currently, there are several standard treatments used to treat prostate cancer including watchful waiting, surgery, radiation therapy, radiopharmaceutical therapy, hormone therapy, chemotherapy, immunotherapy therapy, and bisphosphonate therapy. Immunotherapy is emerging as an effective treatment to prolong overall survival in patients with metastatic castration-resistant prostate cancer. One such immunotherapy is sipuleucel-T, an therapeutic cancer vaccine consisting of autologous peripheral-blood mononuclear cells (PBMCs), including antigen-presenting cells (APCs), that have been activated ex vivo with a recombinant fusion protein (PA2024) as disclosed in the following U.S. Pat. Nos. 6,080,409, 5,976,546, 6,210,662, and 7,413,869, which are each incorporated herein by reference. PA2024 consists of prostatic acid phosphatase, a prostate antigen that is fused to an immune-cell activator, granulocyte-macrophage colony-stimulating factor (Kantoff P W, et al., N Engl J Med. 2010 Jul. 29; 363(5):441-22).

A problem with immunotherapy is that it is difficult to predict which mCRPC subjects would have an increase in overall survival with treatment of sipuleucel-T. Thus, there is a need for molecular biomarkers that are predictive of clinical outcome after treatment with sipuleucel-T using gene expression profiles from PBMCs or other biological samples.

BRIEF SUMMARY OF THE INVENTION

Here is disclosed a method of predicting the overall survival of a subject with mCRPC. The method comprises:
(a) determining a gene expression level of a first biomarker;
(b) determining a gene expression level of at least one additional biomarker different from the first biomarker; and
(c) transforming the expression level of the first biomarker and the at least one additional biomarker into a first score corresponding to a probability of overall survival in response to treatment with sipuleucel-T. The first biomarker is selected from the group consisting of SYNGR3, AURKC, CHI3L2, SNTB1, ZNF268, COL1A1, LAX1, DPPA4, CDK5RAP2, KCNQ5, ZFYVE28, DNAH11, and TAP2. The at least one additional biomarker is selected from the group consisting of SYNGR3, AURKC, CHI3L2, SNTB1, ZNF268, COL1A1, LAX1, DPPA4, CDK5RAP2, KCNQ5, ZFYVE28, DNAH11, and TAP2.

In another aspect, the invention relates to a kit for determining in a biological sample an expression product level of at least one of the genes selected from the group consisting of SYNGR3, AURKC, CHI3L2, SNTB1, ZNF268, COL1A1, LAX1, DPPA4, CDK5RAP2, KCNQ5, ZFYVE28, DNAH11, and TAP2. The kit comprises a plurality of oligonucleotide primers, wherein the plurality of primers consist essentially of at least one pair of oligonucleotide primers for amplification of at least one of the genes selected from the group consisting of SYNGR3, AURKC, CHI3L2, SNTB1, ZNF268, COL1A1, LAX1, DPPA4, CDK5RAP2, KCNQ5, ZFYVE28, DNAH11, and TAP2, wherein the expression product is RNA or cDNA.

In a further aspect, the invention relates to a method of predicting a reduction in risk of death following treatment of a mCRPC subject with sipuleucel-T. The method comprises: (a) converting RNA from a biological sample of the subject to cDNA through reverse transcription; (b) hybridizing the cDNA with a plurality of oligonucleotide primers, wherein said plurality of primers comprises at least one pair of oligonucleotide primers for a gene selected from the group consisting of: SYNGR3, AURKC, CHI132, SNTB1, ZNF268, COL1A1, LAX1, DPPA4, CDK5RAP2, KCNQ5, ZFYVE28, DNAH11, and TAP2; (c) performing PCR on the cDNAs; and (d) determining an increase or decrease of an expression product of at least one tested gene in the biological sample from the subject.

BRIEF DESCRIPTION OF THE SEVERAL VIEWS OF THE DRAWING(S)

FIG. 1: P-value distribution of association of Nanostring gene expression data with overall survival. Left: P-value distribution using combined sipuleucel-T and control arms (Equation 1); p-value of the interaction between treatment and gene expression (i.e. treatment:gene-expression) is plotted. Right: P-value distribution using sipuleucel-T arm only (Equation 2); p-value of gene-expression variable is plotted.

Figure 2:
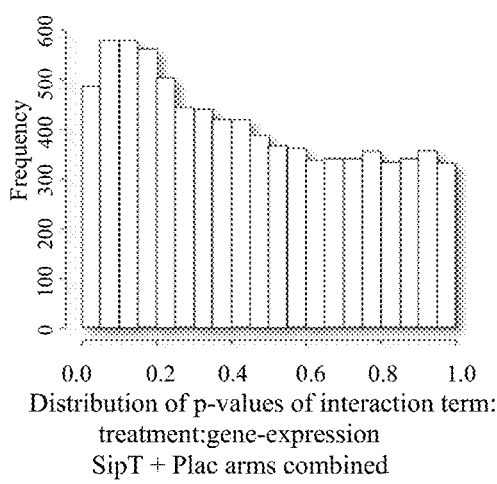
Figure 2:
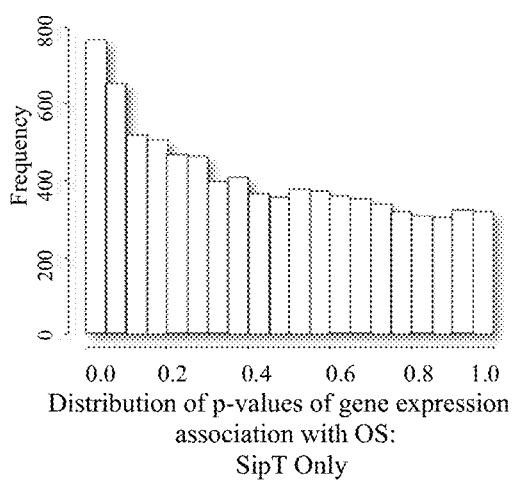

FIG. 2: P-value distribution of association of Affymetrix gene expression data with overall survival. Left: P-value distribution using combined sipuleucel-T and control arms (Equation 1); p-value of the interaction between treatment and gene expression (i.e. treatment:gene-expression) is plotted. Right: P-value distribution using sipuleucel-T arm only (Equation 2); p-value of gene-expression variable is plotted.

Figure 3:
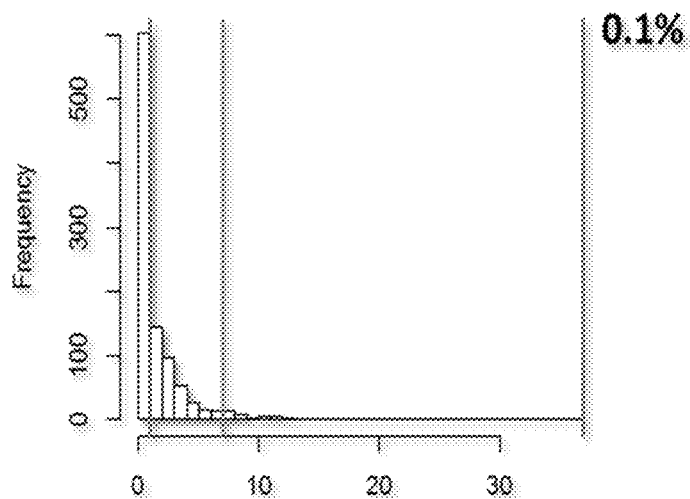

FIG. 3: Histogram of the number of Nanostring gene candidates with 1000 permutations. The first two vertical lines from the left represent the $50^{th}$ and $95^{th}$ percentiles, respectively. The last line indicates the 37 gene candidates that meet the criteria with real data. The probability of selecting 37 gene candidates by chance is 0.01.

Figure 4:
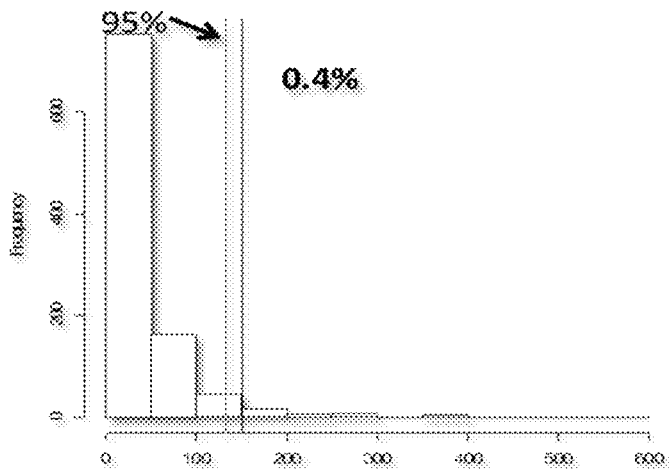

FIG. 4: Histogram of the number of Affymetrix gene candidates with 1000 permutations. The first line on the left represents the $95^{th}$ percentile. The second line from the left indicates the 151 gene candidates that were found in the real data. The probability of selecting 151 gene candidates by chance is 0.04.

Figure 5A:
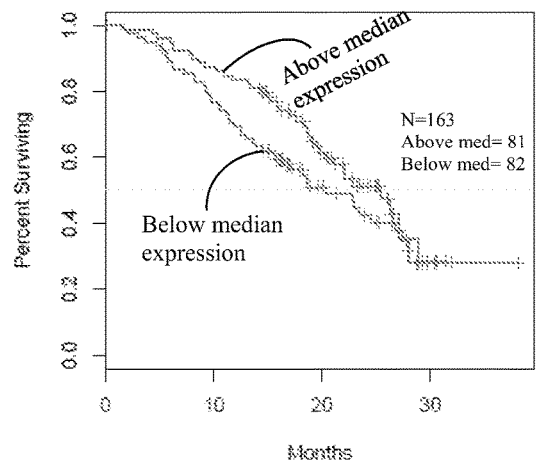

FIG. 5A: Overall survival plot for SNTB1, one of the gene candidates with significant overall survival association in at least one of the qPCR Panels 1, 2, and 3. The P-value of gene expression with overall survival association (in sipuleucel-T arm) is included in the survival plot.

Figure 5B:
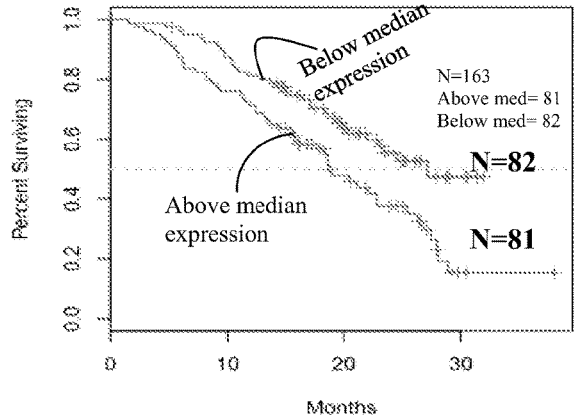

FIG. 5B: Overall survival plot for SYNGR3, one of the gene candidates with significant overall survival association in at least one of the qPCR Panels 1, 2, and 3. The P-value of gene expression with overall survival association (in sipuleucel-T arm) is included in the survival plot.

Figure 5C:
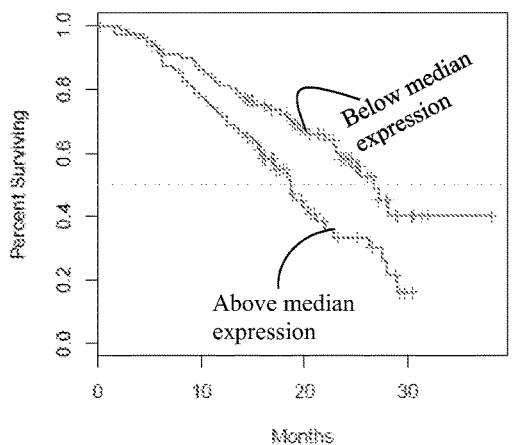

FIG. 5C: Overall survival plot for AURKC, one of the gene candidates with significant overall survival association in at least one of the qPCR Panels 1, 2, and 3. The P-value of gene expression with overall survival association (in sipuleucel-T arm) is included in the survival plot.

Figure 5D:
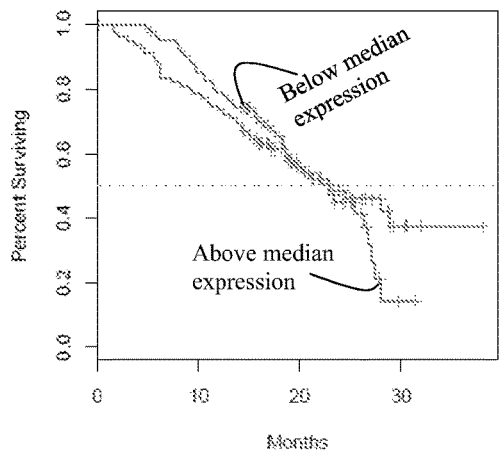

FIG. 5D: Overall survival plot for ZNF268, one of the gene candidates with significant overall survival association in at least one of the qPCR Panels 1, 2, and 3. The P-value of gene expression with overall survival association (in sipuleucel-T arm) is included in the survival plot.

Figure 5E:
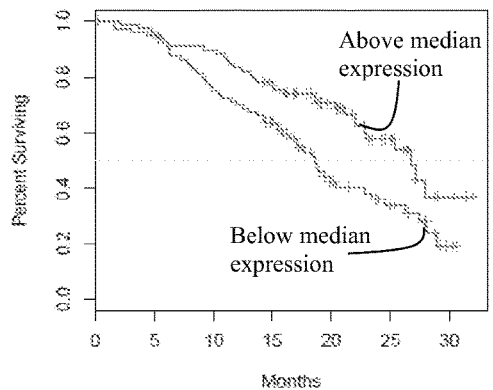

FIG. 5E: Overall survival plot for CHI132, one of the gene candidates with significant overall survival association in at least one of the qPCR Panels 1, 2, and 3. The P-value of gene expression with overall survival association (in sipuleucel-T arm) is included in the survival plot.

Figure 6:
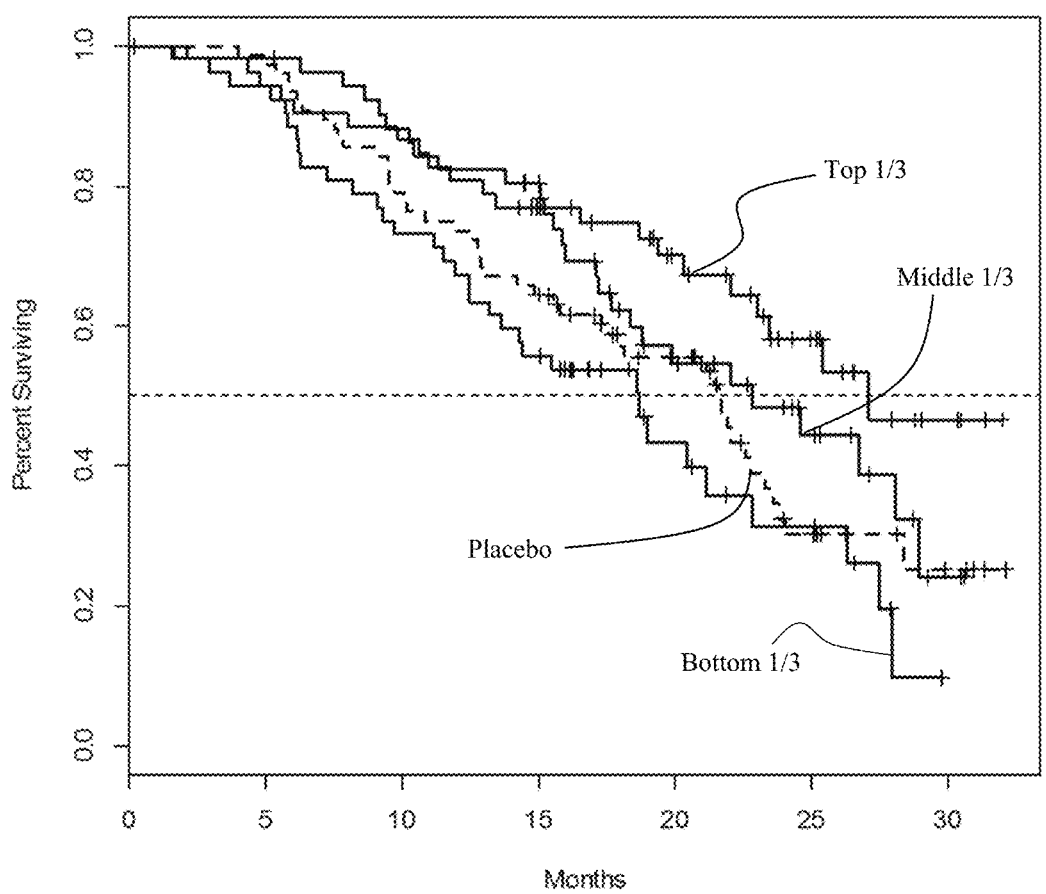

FIG. 6: Kaplan-Meier plot showing survival curves of patient groups described in composite score using Equation (7).

Figure 7:
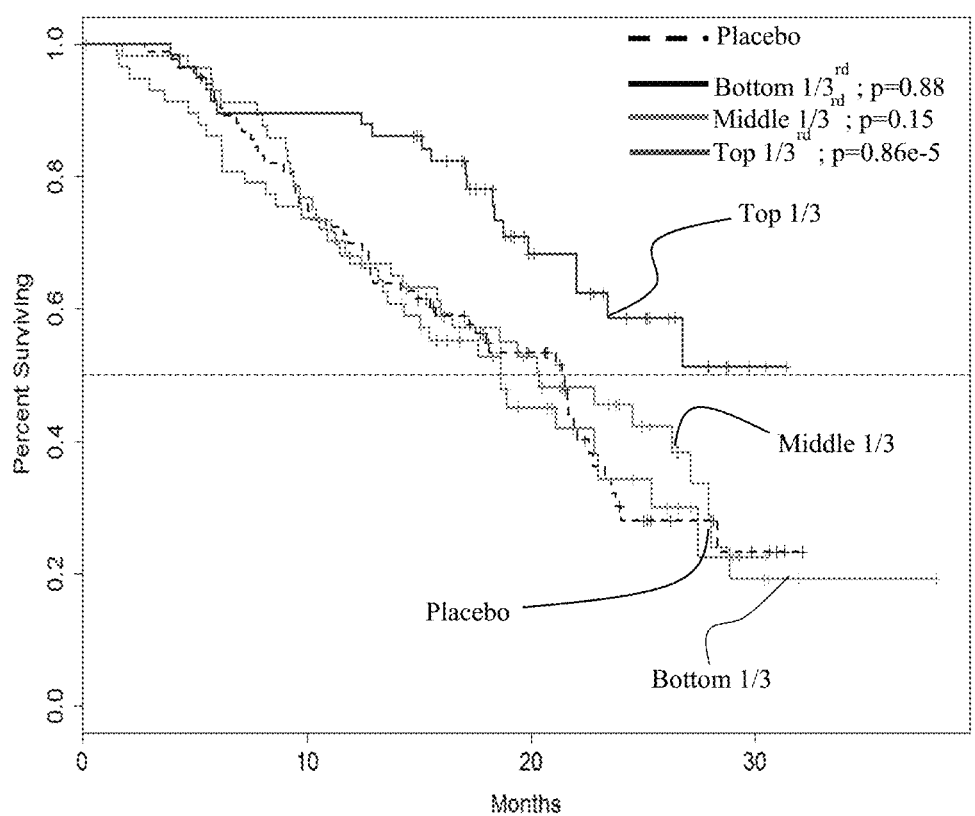

FIG. 7: Kaplan-Meier plot showing survival curves of patient groups described in composite score using Equation (14). The plot shows that patients within the top tertile of composite expression score of Equation (14) in the sipuleucel-T arm were more likely to survive relative to a control group.

DETAILED DESCRIPTION OF THE INVENTION

Novel immune-based cancer therapies continue to emerge as knowledge increases of how specific immune system responses are evoked. These immunotherapies induce anti-tumor immune responses, decrease tumor-load, and can change the course of the disease. Various types of immunotherapies have been developed, including peptide vaccines, DNA/RNA vaccines, cell-based vaccines, and T-cell modulators. (Harm W, et al., *Front Immunol.* 2014; 5: 191).

Among these immunotherapies is sipuleucel-T, an autologous cellular immunotherapy for treatment of advanced prostate cancer. It is manufactured by activating PBMCs, including APCs, with a fusion protein containing prostatic acid phosphatase. (Sheikh N A, et al., *Cancer Immunol Immunother* 2013 62:137-147). The goal of administering sipuleucel-T is improving overall survival. Accordingly, methods and compositions for identifying pre-treatment biomarkers that are predictive of clinical outcome after treatment with sipuleucel-T are provided herein. Such methods include predicting the overall survival of a subject with mCRPC. A kit for determining, in a biological sample, an expression product level of at least one of the genes selected form the group consisting of "SYNGR3," "AURKC," ""ZNF268", "CHI132," "SNTB1," "COL1A1," "LAX1," "DPPA4," "CDK5RAP2," "KCNQ5," "ZFYVE28," "DNAH11," and "TAP2" is also provided. Further, a method of predicting a reduction in risk of death following treatment of sipuleucel-T is provided. A combination of biomarkers for predicting overall survival after treatment with sipuleucel-T is also provided.

All publications, patents, and other references cited herein are hereby incorporated by reference in their entirety in the present disclosure.

Unless otherwise defined, all terms of art, notations and other scientific terminology used herein are intended to have the meaning commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Abbreviations used herein:
APC: antigen-presenting cells
CTC: circulating tumor cell
mCRPC: metastatic castrate-resistant prostate cancer
OS: overall survival
PBMC: peripheral blood mononuclear cells
SVD: Singular Value Decomposition "SYNGR3," "AURKC," ""ZNF268", "CHI132," "SNTB1," "COLA1," "LAX1," "DPPA4," CDK5RAP2," "KCNQ5," "ZFYVE28," "DNAH11," and "TAP2" and other biomarkers recited herein, refer to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98%, or 99% or greater amino acid sequence identity, preferably over a region of over a region of at least about 25, 50, 100, 200, 500, 1000, or more amino acids, to a polypeptide encoded by a referenced nucleic acid or amino acid sequence described herein; (2) specifically binds to antibodies, e.g., polyclonal antibodies, raised against an immunogen comprising a referenced amino acid sequence, immunogenic fragments thereof, and conservatively modified variants thereof; (3) specifically hybridized under stringent hybridization conditions to a nucleic acid encoding a referenced amino acid sequence, and conservatively modified variants thereof; (4) have a nucleic acid sequence that has greater than about 60% nucleotide sequence identity, 65%, 70%, 80%, 85%, 90%, preferably 91%, 92%, 93%, 94%, 95%, 96%, 97%, 98%, or 99% or greater nucleotide sequence identity, preferably over a region of at least about 10, 15, 20, 25, 50, 100, 200, 500, 1000, or more nucleotides, to reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

As used herein, the term "determining" in the context of determining a gene expression level" refers to predicting, identifying, estimating, quantifying, calculating or otherwise deriving the gene expression level of certain genes in a biological sample of a patient.

As used herein, the term "biomarkers" refers to an indicator of a biological state of an organism. The level of a biomarker can be measured to determine the biological state of the organism. Exemplary biomarkers include metabolites and macromolecules such as proteins, carbohydrates and lipids. Biomarkers can indicate the presence of a disease, such as cancer, or the severity of a disease or condition. For example, the presence or absence of a biomarker can be indicative of malignancy, metastasis, or lack thereof. In some cases, the level of one or more biomarkers, or a combination thereof, can indicate disease prognosis, therapeutic response, or predict therapeutic outcome. In other cases, the biomarker is a molecule or a gene (typically protein or nucleic acid such as RNA) that is differentially expressed in a cell, which is useful for indicating disease prognosis, therapeutic response, or predict therapeutic outcome.

As used herein, the term "biological sample" includes whole blood, peripheral blood mononuclear cells (PBMCs), circulating tumor cells (CTCs), and tumor tissue.

As used herein, the term "overall survival" as that term is known in the art refers to time in months or years from date of treatment with sipuleucel-T to death from any cause.

As used herein, the term "primer" as that term is known in the art refers to an oligonucleotide that is complementary to a particular nucleic acid sequence of a template and is capable of acting as a point of initiation of extension with a polymerase under suitable PCR conditions and when used in suitable PCR primer pairs, will produce an amplicon of the target. The primer is preferably single stranded but can also be double stranded. If double stranded, the primer is first treated to separate its strands before being used to prepare extension products. Preferably, the primer is an oligodeoxyribonucleotide. The exact number of nucleotides in the primers will depend on many factors, including temperature, source of primer and the use of the method. The PCR primers of the present invention generally have about 18 to 25 nucleotides but can contain more or less. Methods for the design and synthesis of PCR primers are readily known in the art.

Exemplary Gene Expression Biomarkers for Predicting Overall Survival of a Subject with mCRPC in Response to Treatment with Sipuleucel-T:

SNTB1

SNTB1 is a member of the syntrophin gene family, which contains at least two other structurally-related genes. The protein encoded by this gene is a peripheral membrane protein found associated with dystrophin and syntrophin-related proteins. Dystrophin is a large, rod-like cytoskeletal protein found at the inner surface of muscle fibers. As shown in FIG. 5A, this gene was positively associated with overall survival, (i.e., above median expression of this gene is associated with better survival.) Exemplary SNTB1 sequences are publically available, for example, from GenBank (e.g., accession numbers NC_000008.11, NT_008046.17, NC_01819.2).

SYNGR3

The Synaptogryin 3 (SYNGR3) gene is an integral membrane protein and its gene product belongs to the synaptogryin gene family. The exact function of this protein is uncertain. However, based on studies of similar murine protein, this gene may be a synaptic vesicle protein that also interacts with the dopamine transporter. As shown in FIG. 5B, this gene was negatively associated with overall survival (i.e., median expression of this gene is associated with worse overall survival). Exemplary SYNGR3 sequences are publically available, for example, from GenBank (e.g., accession numbers NC_000016.10, NC_018927.2, NT_010393.17.)

AURKC

The AURKC gene encodes a member of the Aurora subfamily of serine/threonine protein kinases. The encoded protein is a chromosomal passenger protein that forms complexes with Aurora-B and inner centromere proteins and may play a role in organizing microtubules in relation to centrosome/spindle function during mitosis. This gene is overexpressed in several cancer cell lines, suggesting an involvement in oncogenic signal transduction. As shown in FIG. 5C, this gene was negatively associated with overall survival (i.e. above median expression of this gene is associated with worse survival.) Exemplary AURKC sequences are publically available, for example, from GenBank (e.g., accession numbers NC_000019.10, NT_011109.17, NC_018930.2).

ZNF268

The Zinc Finger Protein 268 (ZNF268) gene is a protein coding gene. Among its related pathways are those provided at http://pathcards.genecards.org/card/gene_expression. GO annotations related to this gene include sequence-specific DNA binding transcription factor activity. As shown in FIG. 5D, this gene was negatively associated with overall survival (i.e., above median expression of this gene is associated with worse survival). Exemplary ZNF268 sequences are publically available, for example, from GenBank (e.g., accession numbers NC_000012.12, NC_018923.2, NT_024477.15).

CHI132

The Chitinase 3-Like 2 (CHI132) gene encodes a protein that is similar to bacterial chitinases but lacks chitinase activity. The encoded protein is secreted and is involved in cartilage biogenesis. As shown in FIGS. 5E, this gene was positively associated with overall survival, (i.e., above median expression of this gene is associated with better survival). Exemplary CHI132 sequences are publically available, for example, from GenBank (e.g., accession numbers NC_000001.11, NC_018912.2, NT_032977.10).

COL1A1

The Collagen, Type 1, Alpha 1 (COL1A1) gene encodes the pro-alpha1 chains of type I collagen whose triple helix comprises two alpha1 chains and one alpha2 chain. Type I is a fibril-forming collagen found in most connective tissues and is abundant in bone, cornea, dermis and tendon. Mutations in this gene are associated with osteogenesis imperfecta types I-IV, Ehlers-Danlos syndrome type VIIA, Ehlers-Danlos syndrome Classical type, Caffey Disease and idiopathic osteoporosis. This gene was negatively associated with overall survival (i.e., above median expression of this gene is associated with worse survival). Exemplary COL1A1 sequences are publically available, for example, from GenBank (e.g., accession numbers NC_000017.11, NT)010783.16, NC_08928.2).

LAX1

Lymphocyte Transmembrane Adaptor 1 (LAX1) is a Protein Coding gene. Diseases associated with LAX1 include blepharochalasis and chondromalacia. GO annotations related to this gene include protein kinase binding and SH2 domain binding. This gene is known to negatively regulate TCR (T-cell antigen receptor)-mediated signaling in T-cells and BCR (B-cell antigen receptor)-mediated signaling in B-cells. This gene was positively associated with overall survival, (i.e., above median expression of this gene is associated with better survival). Exemplary LAX1 sequences are publically available, for example, from GenBank (e.g., accession numbers NC000001.11, NT_004487.20, NC_018912.2).

DPPA4

Developmental Pluripotency Associated 4 (DPPA4) is a protein coding gene. An important paralog of this gene is DPPA2. May be involved in the maintenance of active epigenetic status of target genes. May inhibit differentiation of embryonic cells into a primitive ectoderm lineage. This gene was positively associated with overall survival, (i.e., above median expression of this gene is associated with better survival). Exemplary DPPA4 sequences are publically available, for example, from GenBank (e.g., accession numbers NC_000003.12, NT_005612.17, NC_018914.2).

CDK5RAP2

CDK5 Regulatory Subunit Associated Protein 2 (CDK5RAP2) is a gene that encodes a regulator of CDK5 (cyclin-dependent kinase 5) activity. The protein encoded by this gene is localized to the centrosome and Golgi complex, interacts with CDK5R1 and pericentrin (PCNT), plays a role in centriole engagement and microtubule nucleation, and has been linked to primary microcephaly and Alzheimer's disease. This gene was negatively associated with overall survival (i.e., above median expression of this gene is associated with worse survival). Exemplary CDK5RAP2 sequences are publically available, for example, from GenBank (e.g., accession numbers NC_000009.12, NT_008470.20, NC_018920.2).

KCNQ5

The Potassium Channel, Voltage Gated KQT-Like Subfamily Q, Member 5) (KCNQ5) gene is a member of the KCNQ potassium channel gene family that is differentially expressed in subregions of the brain and in skeletal muscle. The protein encoded by this gene yields currents that activate slowly with depolarization and can form heteromeric channels with the protein encoded by the KCNQ3 gene. Currents expressed from this protein have voltage dependences and inhibitor sensitivities in common with M-currents. They are also inhibited by M1 muscarinic receptor activation. Multiple transcript variants encoding different isoforms have been found for this gene. This gene was positively associated with overall survival, (i.e., above median expression of this gene is associated with better survival).). Exemplary KCNQ5 sequences are publically available, for example, from GenBank (e.g., accession numbers NC_000006.12, NT_025741.16, NC_018917.2).

ZFYVE28

The Zinc Finger, FYVE Domain Containing 28 (ZFYVE28) gene is a Protein Coding gene. Among its related pathways are Internalization of ErbB1. GO annotations related to this gene include phosphatidylinositol-3-phosphate binding. Negative regulator of epidermal growth factor receptor (EGFR) signaling. Acts by promoting EGFR degradation in endosomes when not monoubiquitinated. This gene was positively associated with overall survival, (i.e., above median expression of this gene is associated with better survival). Exemplary ZFYVE28 sequences are publically available, for example, from GenBank (e.g., accession numbers NC_000004.12, NT_006051.19, NC_018915.2).

DNAH11

The Dynein, Axonemal, Heavy Chain 11 (DNAH11) gene encodes a ciliary outer dynein arm protein and is a member of the dynein heavy chain family. It is a microtubule-dependent motor ATPase and has been reported to be involved in the movement of respiratory cilia. Mutations in this gene have been implicated in causing Kartagener Syndrome (a combination of situs inversus totalis and Primary Ciliary Dyskinesia (PCD), also called Immotile Cilia Syndrome 1 (ICS1)) and male sterility. This gene was positively associated with overall survival, (i.e., above median expression of this gene is associated with better survival). Exemplary DNAH11 sequences are publically available, for example, from GenBank (e.g., accession numbers NC_000007.14, NC_018918.2, NT_007819.18).

TAP2

The membrane-associated protein encoded by the Transporter 2, ATP-Binding Cassette, Sub-Family B (MDR/TAP) (TAP2) gene is a member of the superfamily of ATP-binding cassette (ABC) transporters. ABC proteins transport various molecules across extra- and intra-cellular membranes. ABC genes are divided into seven distinct subfamilies (ABC1, MDR/TAP, MRP, ALD, OABP, GCN20, White). This protein is a member of the MDR/TAP subfamily. Members of the MDR/TAP subfamily are involved in multidrug resistance. This gene is located 7 kb telomeric to gene family member ABCB2. The protein encoded by this gene is involved in antigen presentation. This protein forms a heterodimer with ABCB2 in order to transport peptides from the cytoplasm to the endoplasmic reticulum. Mutations in this gene may be associated with ankylosing spondylitis, insulin-dependent diabetes mellitus, and celiac disease. This gene was negatively associated with overall survival (i.e., above median expression of this gene is associated with worse survival). Exemplary TAP2 sequences are publically available, for example, from GenBank (e.g., accession numbers NC_000006.12, NC_018917.2, NT_007592.16, NT_113891.3, NT_167244.2, NT_167245.2, NT_167246.2, NT_167247.2, NT_167248.2, NT_167249.2).

The following examples are given for illustrative purposes only and are not intended to be limited unless otherwise specified. It should be appreciated by those of skill in the art that the techniques disclosed in the examples which follow represent techniques discovered by the inventors to function well in the practice of invention, and thus can be considered to constitute preferred modes for its practice. Those of skill in the art should appreciate that many changes can be made in the specific embodiments which are disclosed and still obtain a like or similar result without departing from the spirit and scope of the invention.

Example 1: Sipuleucel-T Treatment of Subjects

In a randomized, placebo-controlled trial involving 512 subjects enrolled in an Immunotherapy for Prostate Adenocarcinoma Treatment (IMPACT) study, conducted in accordance with applicable regulations of the FDA and the Good Clinical Practice guidelines of the International Conference on Harmonization, men with mCRPC were randomized 2:1 to receive sipuleucel-T or control. To prepare the sipuleucel-T, freshly obtained leukapheresis PBMCs were prepared with PA2024 for 36-44 hours at 37° C. To prepare the control, approximately one-third of PBMCs were prepared without PA2024 and the remainder of the cells was cryopreserved for later use. Subjects received sipuleucel-T or control as an intravenous infusion over 30-60 minutes approximately every 2 weeks for a total of three infusions. As a result of the IMPACT study, 257 baseline (pre-sipuleucel-T treatment) PBMC samples were available from IMPACT; RNAs were extracted from these samples and evaluated.

Example 2: Gene Expression Profiles from PBMCs in IMPACT

The pre-treatment gene expression profiles of pre-sipuleucel-T PMBC samples were analyzed using Affymetrix Hgu133 plus2 microarrays and NanoString Immunology nCounter assays. Specifically, IMPACT baseline (pre-treatment, BASIM) PBMC samples were used for RNA extraction and gene expression profiling. Data collection, normalization, analyses, and prioritization of candidate markers for confirmation were performed using PrimePCR™. RNA extraction was performed with the QiaShredder reagent to ensure maximum RNA yield and quality. RNA samples that passed RNA Quality Control (QC) metrics for DNA microarray hybridization were selected using the following criteria: (i) RNA Integrity Number greater than 5; and (ii) electropherogram has 2 clear peaks without noise. The Agilent Bioanalyzer traces and 28S/18S ratio may also be used. In each sample, 50 ng of RNA was amplified using the NuGen Ovation WB (whole blood) target labeling and amplification protocol.

Although gene expression profiles from PBMC samples were evaluated and analyzed, it should be appreciated that alternative approaches, such as protein levels (from serum or PBMCs) may also be relevant for this purpose.

Affymetrix Profile QC

To assess array profiling quality, outlier detection methods were used based on the ArrayQualityMetrics R/Bioconductor package. Profiling samples were considered poor quality if they were flagged as outliers by three or more of the six methods used within ArrayQualityMetrics. All samples which failed profiling QC were re-profiled using the same RNA.

Nanostring Profile QC

NSolver is software provided by NanoString for data QC and normalization. nSolver uses 6 positive controls and 15 reference (housekeeping) genes from the data for normalization. The 15 reference genes are ABCF1, ALAS1, EEF1G, G6PD, GAPDH, GUSB, HPRT1, OAZ1, POLR1B, POLR2A, PPIA, RPL19, SDHA, TBP and TUBB. The positive controls can be used to normalize platform associated sources of variation (e.g. hybridization conditions) according to the nCounter_Gene_Expression_Data_Analysis_Guildines.pdf. The positive control scaling factor has a normal range of 0.3-3 and is flagged if it falls outside this range. Reference (housekeeping) gene normalization was done after positive control normalization and corrects for differences in sample input between different lanes in a cartridge. nSolver calculates a reference genes scaling factor called content normalization factor. A normal range of 0.2-3 was used for the content normalization factor to filter good samples and any samples outside this range were flagged as outliers. Using positive and content normalization flags, two outlier samples were removed (with patient IDs 92162-0673 and 92027-1274) and the remaining 251 samples were used for further analysis.

Affymetrix and Nanostring Platform Data Normalization and Adjustments for Technical Batch Effects Normalization Samples processed and profiled in multiple batches may be confounded by systematic errors called batch effects. In order to determine which batch effect factors to adjust for, the association of all technical factors was tested.

Using Singular Value Decomposition analysis, five principal components were found to explain 95% of the variation within Affymetrix data. Four out of the five principal components were associated with technical factors with a significance of p<0.05. Four principal components (known as Eigengenes in SVD) were correlated with the technical factors: PBMC processing site after the blood draw, PBMC processing date, RNA integrity number (RIN score), and RNA profiling batch (in this case, it corresponds to the RNA amplification plate number, prior to Affymetrix array hybridization). (See Alter O, Brown P O, Botstein D., Singular value decomposition for genome-wide expression data processing and modeling, Proc Natl Acad Sci USA, 2000 Aug. 29; 97(18):10101-6, at http://www.ncbi.nlm.nih.gov/pubmed/10963673).

Since PBMC processing site and PBMC processing date were dependent variables, and adjusting for one of these variables would adjust for the other, PBMC processing date was selected for the Affymetrix data.

With respect to the nSolver normalized gene expression data, in order to determine which batch effects factors to adjust for, the following association of all technical factors were tested with nSolver normalized gene expression data, namely, site of PBMC processing after the blood draws, PBMC processing date, RNA integrity number (RIN score), RNA profiling batch, Nanostring cartridge lane number and Nanostring binding density.

Using Singular Value Decomposition analysis, four principal components collectively explain 95% of the variation within Nanostring data. All the four principal components were associated with technical factors with a significance <0.05. These four Eigengenes are associated with PBMC processing site, PBMC processing date, RIN, RNA profiling batch and Nanostring binding density in nSolver-normalized gene expression data. Since PBMC processing site and PBMC processing date were dependent variables, and adjusting for one of these variables would adjust for the other, the PBMC processing date was chosen. After nSolver normalization, the expression levels were adjusted for RNA integrity number (RIN), RNA profiling batch (two batches Nanostring batch and UW batch) and PBMC processing date (as a splines function with 6 degrees of freedom). Adjusting for binding density would nullify the effects of normalization, and therefore, the expression levels were not adjusted for binding density.

Robust Multi-array Average (RMA) is a common normalization approach. After the normalization of the data using RMA, the data was adjusted for technical factors—PBMC processing date (as a splines function with six degrees of freedom), RIN score and RNA profiling batch (or Array plate).

In another approach, probe-level adjustment and summarization (PLAS), then probe-level intensities were first adjusted to the same median intensities and then they were adjusted for the technical batch effects described supra. (Mecharn, B. H. Nelson, P. S. & Storey, J. D. Supervised normalization of microarrays. *Bioinformatics* 26, 1308-1315 (2010). The adjusted probe-level intensities for each probe-set were then summarized using a weighted average; weights of the probes being proportional to the r-square value of the association of the probe intensities to the average intensity across all the probes in a probe-set. A higher average correlation between genes across the Affymetrix and Nanostring platforms was observed using PLAS compared to RMA. Thus, PLAS normalized data was used for further analysis.

The probe filtering was based on the table of the first three singular values for each probe set based on Singular Value Decomposition method. The following steps were performed: (1) select all probe sets with the first eigenvalue equal or larger than 0.5 (50% of the variance explained); and (2) remove all probe sets which don't have a corresponding Entrez Gene ID. Probe sets which map to the same Entrez IDs were kept with the larger first eigenvalue. The probes were further filtered for non-specific binding probes and GO annotations.

Statistical Analysis: Association of Gene Expression Profiles with Overall Survival Using Cox Models Association of gene expression levels with overall survival was performed using a multivariate Cox proportional hazards regression model, where overall survival was fit to the gene expression variable along with prognostic factors described by Halabi et. al. (Halabi, S., et al., Prognostic model for predicting survival in men with hormone-refractory metastatic prostate cancer. *J Clin Oncol*, 2003. 21(7): p. 1232-7.) These prognostic factors include the following: PSA (log), LDH (log), Alkaline phosphatase (log), Hemoglobin, Total Gleason score (≤7, >7), and ECOG status (0, 1). Overall survival associations were only reported for the treatment:gene-expression interaction (Equation (1)), or the gene expression variable (Equation (2)) using Wald's test. A likelihood ratio test was also performed to determine the improvement of fit to overall survival due to gene-expression variable by comparing the full models (as given in Equations (1) and (2)) to the base model (Cox model using only the prognostic variables from Halabi nomogram, Equation (3)). No adjustments of the p-values were made for multiple testing.

Association of gene expression with overall survival was performed using the following methods:

Combined analysis of sipuleucel-T and control arms: In the survival fit, along with the prognostic factors, an interaction factor between treatment arm (sipuleucel-T and control) and gene expression measures was included. The overall survival model used was:

Survival~PSA+LDH+Alkaline phosphatase+Hemoglobin+Total Gleason score+ECOG status+ GENE-EXPRESSION(log)*TREATMENT ARM        Equation (1)

Separate analysis of sipuleucel-T arm: In the survival fit, along with the prognostic factors, gene expression measures from sipuleucel-T arm only were included. The overall survival model used was:

Survival~PSA+LDH+Alkaline phosphatase+Hemoglobin+Total Gleason score+ECOG status+ GENE-EXPRESSION(log)        Equation (2)

The base model used was:

Survival~PSA+LDH+Alkaline phosphatase+Hemoglobin+Total Gleason score+ECOG status        Equation (3)

The overall survival associations with all the gene expression values for the sipuleucel-T arm, control arm, and both arm interactions for Affymetrix and Nanostring are provided in the following Tables:

TABLE 1

Affymetrix Single Arm and Interaction Association with 151 genes

| | Combined Sip-T + Control arm OS association | | | Sipuleucel-T arm OS association | | | | |
|---|---|---|---|---|---|---|---|---|
| GENE NAME | Expression P Value | Interaction p-value | Log Likelihood Ratio | Expression P Value | Hazard Ratio (lower limit) | Hazard Ratio (upper limit) | Expression P value | Log Likelihood Ratio |
| THBS1 | 0.008 | 0.000 | 0.002 | 1.439 | 1.05 | 1.97 | 0.023 | 0.019 |
| CEP57L1 | 0.049 | 0.001 | 0.002 | 0.308 | 0.14 | 0.66 | 0.002 | 0.002 |
| SYNGR3 | 0.038 | 0.001 | 0.001 | 1.874 | 1.23 | 2.87 | 0.004 | 0.005 |
| BYSL | 0.010 | 0.001 | 0.004 | 2.253 | 1.06 | 4.79 | 0.035 | 0.040 |
| FARS2 | 0.018 | 0.002 | 0.009 | 0.558 | 0.31 | 0.99 | 0.046 | 0.045 |
| NTSR1 | 0.045 | 0.002 | 0.003 | 2.193 | 1.26 | 3.81 | 0.005 | 0.008 |
| SLC25A32 | 0.126 | 0.003 | 0.007 | 3.050 | 1.36 | 6.83 | 0.007 | 0.006 |
| TDRKH | 0.060 | 0.003 | 0.007 | 0.291 | 0.11 | 0.77 | 0.013 | 0.010 |
| PEX13 | 0.093 | 0.003 | 0.006 | 2.808 | 1.33 | 5.92 | 0.007 | 0.007 |
| DXO | 0.051 | 0.003 | 0.011 | 0.379 | 0.17 | 0.83 | 0.015 | 0.016 |
| C10orf2 | 0.048 | 0.004 | 0.009 | 2.048 | 1.12 | 3.75 | 0.020 | 0.024 |
| SNTB1 | 0.085 | 0.004 | 0.010 | 0.526 | 0.32 | 0.85 | 0.009 | 0.010 |
| NIT2 | 0.106 | 0.004 | 0.007 | 0.308 | 0.13 | 0.71 | 0.006 | 0.006 |
| NSRP1 | 0.220 | 0.004 | 0.005 | 5.026 | 1.71 | 14.76 | 0.003 | 0.003 |
| DNAI2 | 0.047 | 0.004 | 0.013 | 0.339 | 0.13 | 0.91 | 0.031 | 0.026 |
| FOXP4 | 0.080 | 0.004 | 0.011 | 1.975 | 1.14 | 3.42 | 0.015 | 0.016 |
| ABCC5 | 0.119 | 0.004 | 0.010 | 0.593 | 0.40 | 0.87 | 0.008 | 0.008 |
| HEXDC | 0.361 | 0.004 | 0.003 | 0.279 | 0.13 | 0.59 | 0.001 | 0.001 |
| GNA12 | 0.068 | 0.005 | 0.012 | 1.770 | 1.10 | 2.85 | 0.019 | 0.018 |
| PSME1 | 0.057 | 0.005 | 0.014 | 0.235 | 0.07 | 0.81 | 0.022 | 0.021 |
| TTLL5 | 0.082 | 0.005 | 0.008 | 0.376 | 0.19 | 0.75 | 0.006 | 0.007 |
| SLK | 0.242 | 0.005 | 0.009 | 3.541 | 1.44 | 8.73 | 0.006 | 0.006 |
| NR1D2 | 0.363 | 0.005 | 0.004 | 2.202 | 1.32 | 3.66 | 0.002 | 0.002 |
| ZNF615 | 0.107 | 0.005 | 0.013 | 2.153 | 1.16 | 3.98 | 0.015 | 0.015 |
| UBXN8 | 0.225 | 0.005 | 0.003 | 0.247 | 0.10 | 0.58 | 0.001 | 0.001 |
| NUP93 | 0.062 | 0.005 | 0.017 | 2.665 | 1.04 | 6.85 | 0.042 | 0.040 |
| HS3ST1 | 0.048 | 0.006 | 0.017 | 1.263 | 1.01 | 1.57 | 0.037 | 0.038 |
| TRIM16 | 0.124 | 0.006 | 0.012 | 0.308 | 0.13 | 0.75 | 0.010 | 0.010 |
| VPS53 | 0.085 | 0.006 | 0.005 | 1.643 | 1.16 | 2.33 | 0.005 | 0.008 |
| RUSC1 | 0.099 | 0.007 | 0.021 | 0.362 | 0.15 | 0.89 | 0.026 | 0.026 |
| GLS2 | 0.117 | 0.008 | 0.017 | 0.319 | 0.12 | 0.82 | 0.018 | 0.014 |
| EMR3 | 0.162 | 0.008 | 0.014 | 0.511 | 0.29 | 0.89 | 0.019 | 0.018 |
| DSEL | 0.430 | 0.008 | 0.003 | 0.198 | 0.07 | 0.54 | 0.002 | 0.001 |
| TSC2 | 0.134 | 0.008 | 0.019 | 0.300 | 0.12 | 0.78 | 0.014 | 0.013 |
| LDLRAP1 | 0.094 | 0.008 | 0.026 | 0.564 | 0.33 | 0.95 | 0.032 | 0.031 |
| SEPW1 | 0.098 | 0.009 | 0.025 | 0.428 | 0.20 | 0.90 | 0.026 | 0.026 |
| BBS9 | 0.288 | 0.009 | 0.009 | 0.374 | 0.19 | 0.73 | 0.004 | 0.003 |
| BCOR | 0.109 | 0.009 | 0.024 | 1.715 | 1.07 | 2.75 | 0.025 | 0.025 |
| EPS8L2 | 0.081 | 0.010 | 0.026 | 0.391 | 0.16 | 0.98 | 0.045 | 0.039 |
| HSCB | 0.086 | 0.010 | 0.023 | 0.461 | 0.22 | 0.95 | 0.036 | 0.035 |
| PRIM2 | 0.062 | 0.010 | 0.030 | 0.537 | 0.29 | 0.99 | 0.048 | 0.048 |
| AURKC | 0.691 | 0.011 | 0.001 | 4.962 | 2.22 | 11.11 | 0.000 | 0.000 |
| CEP41 | 0.197 | 0.011 | 0.016 | 0.496 | 0.29 | 0.85 | 0.010 | 0.010 |

TABLE 1-continued

Affymetrix Single Arm and Interaction Association with 151 genes

| | Combined Sip-T + Control arm OS association | | | Sipuleucel-T arm OS association | | | | |
|---|---|---|---|---|---|---|---|---|
| GENE NAME | Expression P Value | Interaction p-value | Log Likelihood Ratio | Expression P Value | Hazard Ratio (lower limit) | Hazard Ratio (upper limit) | Expression P value | Log Likelihood Ratio |
| AKT3 | 0.165 | 0.011 | 0.029 | 0.476 | 0.25 | 0.92 | 0.026 | 0.026 |
| SYTL1 | 0.461 | 0.012 | 0.004 | 0.358 | 0.19 | 0.67 | 0.001 | 0.001 |
| ZNF180 | 0.166 | 0.012 | 0.030 | 2.711 | 1.13 | 6.51 | 0.026 | 0.029 |
| SUPT16H | 0.122 | 0.012 | 0.033 | 2.135 | 1.02 | 4.48 | 0.045 | 0.046 |
| CMTR2 | 0.140 | 0.012 | 0.031 | 1.866 | 1.05 | 3.31 | 0.033 | 0.034 |
| EIF2S1 | 0.149 | 0.013 | 0.022 | 1.925 | 1.09 | 3.40 | 0.024 | 0.021 |
| UBOX5 | 0.232 | 0.013 | 0.018 | 3.356 | 1.24 | 9.06 | 0.017 | 0.017 |
| SLC9A6 | 0.336 | 0.013 | 0.019 | 2.397 | 1.21 | 4.74 | 0.012 | 0.012 |
| TMEM91 | 0.203 | 0.014 | 0.035 | 0.581 | 0.36 | 0.95 | 0.030 | 0.030 |
| NAA50 | 0.140 | 0.014 | 0.042 | 2.226 | 1.03 | 4.81 | 0.042 | 0.042 |
| ATG4C | 0.182 | 0.014 | 0.019 | 0.369 | 0.16 | 0.87 | 0.023 | 0.016 |
| ROBO3 | 0.504 | 0.014 | 0.010 | 0.425 | 0.24 | 0.76 | 0.004 | 0.003 |
| RAB24 | 0.185 | 0.015 | 0.039 | 0.574 | 0.35 | 0.95 | 0.031 | 0.031 |
| DHX33 | 0.285 | 0.015 | 0.021 | 2.451 | 1.18 | 5.11 | 0.017 | 0.016 |
| HNRNPR | 0.217 | 0.015 | 0.045 | 2.754 | 1.04 | 7.28 | 0.041 | 0.039 |
| COX15 | 0.142 | 0.015 | 0.031 | 0.553 | 0.32 | 0.95 | 0.031 | 0.028 |
| PKP4 | 0.187 | 0.016 | 0.028 | 0.524 | 0.30 | 0.90 | 0.020 | 0.019 |
| NKAP | 0.342 | 0.016 | 0.017 | 3.518 | 1.35 | 9.19 | 0.010 | 0.010 |
| ZKSCAN5 | 0.208 | 0.016 | 0.028 | 2.313 | 1.09 | 4.89 | 0.028 | 0.027 |
| USP9X | 0.301 | 0.016 | 0.021 | 3.055 | 1.29 | 7.25 | 0.011 | 0.012 |
| C14orf159 | 0.221 | 0.016 | 0.029 | 0.559 | 0.35 | 0.89 | 0.015 | 0.015 |
| IMMP2L | 0.197 | 0.017 | 0.040 | 0.469 | 0.23 | 0.96 | 0.038 | 0.038 |
| ZNF268 | 0.483 | 0.017 | 0.003 | 3.558 | 1.66 | 7.61 | 0.001 | 0.002 |
| BSPRY | 0.127 | 0.017 | 0.037 | 0.461 | 0.22 | 0.96 | 0.039 | 0.035 |
| KDELR2 | 0.159 | 0.017 | 0.035 | 0.693 | 0.49 | 0.97 | 0.032 | 0.032 |
| SCAF8 | 0.343 | 0.017 | 0.032 | 3.116 | 1.25 | 7.76 | 0.015 | 0.015 |
| ETV5 | 0.233 | 0.017 | 0.022 | 1.313 | 1.06 | 1.62 | 0.012 | 0.012 |
| IFT27 | 0.321 | 0.018 | 0.019 | 0.574 | 0.38 | 0.86 | 0.007 | 0.007 |
| FBXO22 | 0.145 | 0.018 | 0.029 | 0.459 | 0.23 | 0.92 | 0.029 | 0.027 |
| VEZT | 0.373 | 0.018 | 0.016 | 2.555 | 1.33 | 4.92 | 0.005 | 0.006 |
| COMMD6 | 0.283 | 0.018 | 0.021 | 0.424 | 0.23 | 0.78 | 0.006 | 0.007 |
| PSTPIP1 | 0.247 | 0.019 | 0.034 | 0.563 | 0.35 | 0.90 | 0.017 | 0.018 |
| ADHFE1 | 0.245 | 0.019 | 0.034 | 0.495 | 0.27 | 0.89 | 0.019 | 0.019 |
| INPP4B | 0.240 | 0.019 | 0.031 | 0.574 | 0.36 | 0.92 | 0.022 | 0.020 |
| SFXN2 | 0.444 | 0.019 | 0.006 | 0.330 | 0.16 | 0.68 | 0.002 | 0.002 |
| NUDT5 | 0.152 | 0.020 | 0.040 | 0.458 | 0.22 | 0.96 | 0.039 | 0.037 |
| VILL | 0.269 | 0.020 | 0.031 | 0.400 | 0.19 | 0.83 | 0.014 | 0.015 |
| RAB3GAP1 | 0.351 | 0.020 | 0.009 | 3.016 | 1.44 | 6.33 | 0.004 | 0.004 |
| SMYD2 | 0.213 | 0.020 | 0.041 | 0.522 | 0.30 | 0.92 | 0.023 | 0.024 |
| PRKCE | 0.318 | 0.020 | 0.040 | 0.417 | 0.19 | 0.93 | 0.032 | 0.028 |
| CBR4 | 0.156 | 0.020 | 0.039 | 0.558 | 0.32 | 0.97 | 0.038 | 0.031 |
| CYTH2 | 0.718 | 0.021 | 0.002 | 0.415 | 0.25 | 0.68 | 0.001 | 0.000 |
| ZNF629 | 0.248 | 0.021 | 0.043 | 1.955 | 1.07 | 3.56 | 0.028 | 0.030 |
| AKR7A3 | 0.312 | 0.022 | 0.028 | 0.331 | 0.14 | 0.80 | 0.014 | 0.014 |
| SLC18A2 | 0.253 | 0.022 | 0.035 | 0.466 | 0.23 | 0.93 | 0.030 | 0.030 |
| ACOT13 | 0.420 | 0.022 | 0.023 | 0.457 | 0.25 | 0.82 | 0.009 | 0.008 |
| MLLT6 | 0.455 | 0.023 | 0.026 | 0.445 | 0.24 | 0.82 | 0.009 | 0.009 |
| MUM1 | 0.533 | 0.023 | 0.006 | 0.541 | 0.37 | 0.79 | 0.001 | 0.001 |
| TMEM119 | 0.558 | 0.023 | 0.012 | 2.571 | 1.33 | 4.97 | 0.005 | 0.006 |
| B3GALTL | 0.387 | 0.023 | 0.009 | 1.856 | 1.21 | 2.86 | 0.005 | 0.005 |
| RIN1 | 0.296 | 0.024 | 0.031 | 2.266 | 1.14 | 4.50 | 0.019 | 0.019 |
| CHI3L2 | 0.724 | 0.024 | 0.013 | 0.398 | 0.20 | 0.78 | 0.007 | 0.004 |
| RRP36 | 0.682 | 0.024 | 0.023 | 2.694 | 1.22 | 5.95 | 0.014 | 0.015 |
| SEMA7A | 0.301 | 0.025 | 0.034 | 2.241 | 1.16 | 4.32 | 0.016 | 0.016 |
| OXTR | 0.314 | 0.025 | 0.036 | 0.504 | 0.26 | 0.96 | 0.038 | 0.032 |
| HEMK1 | 0.538 | 0.025 | 0.023 | 0.396 | 0.21 | 0.76 | 0.005 | 0.005 |
| MRTO4 | 0.258 | 0.025 | 0.036 | 2.475 | 1.17 | 5.22 | 0.017 | 0.019 |
| UTP3 | 0.297 | 0.025 | 0.040 | 3.201 | 1.15 | 8.88 | 0.025 | 0.025 |
| ABCA7 | 0.497 | 0.026 | 0.024 | 0.445 | 0.24 | 0.82 | 0.010 | 0.009 |
| STARD13 | 0.239 | 0.026 | 0.050 | 2.191 | 1.09 | 4.40 | 0.028 | 0.032 |
| CNTLN | 0.392 | 0.027 | 0.022 | 0.440 | 0.23 | 0.84 | 0.013 | 0.012 |
| DHPS | 0.338 | 0.027 | 0.038 | 0.485 | 0.26 | 0.89 | 0.020 | 0.018 |
| STK36 | 0.209 | 0.027 | 0.048 | 0.463 | 0.23 | 0.94 | 0.033 | 0.033 |
| POLH | 0.639 | 0.027 | 0.013 | 2.816 | 1.38 | 5.73 | 0.004 | 0.006 |
| NFE2L1 | 0.410 | 0.028 | 0.040 | 2.347 | 1.13 | 4.89 | 0.023 | 0.022 |
| ARL10 | 0.388 | 0.028 | 0.030 | 0.542 | 0.33 | 0.88 | 0.013 | 0.012 |
| TMEM116 | 0.260 | 0.028 | 0.039 | 0.496 | 0.28 | 0.89 | 0.018 | 0.018 |
| SYN1 | 0.178 | 0.028 | 0.044 | 1.403 | 1.04 | 1.89 | 0.027 | 0.029 |
| SDS | 0.238 | 0.028 | 0.043 | 2.072 | 1.15 | 3.73 | 0.015 | 0.022 |
| ZNF584 | 0.358 | 0.028 | 0.049 | 2.751 | 1.16 | 6.53 | 0.022 | 0.024 |

TABLE 1-continued

Affymetrix Single Arm and Interaction Association with 151 genes

| | Combined Sip-T + Control arm OS association | | | Sipuleucel-T arm OS association | | | | |
|---|---|---|---|---|---|---|---|---|
| GENE NAME | Expression P Value | Interaction p-value | Log Likelihood Ratio | Expression P Value | Hazard Ratio (lower limit) | Hazard Ratio (upper limit) | Expression P value | Log Likelihood Ratio |
| INPP5A | 0.300 | 0.028 | 0.029 | 2.893 | 1.24 | 6.75 | 0.014 | 0.013 |
| ASB9 | 0.888 | 0.029 | 0.003 | 0.222 | 0.09 | 0.57 | 0.002 | 0.001 |
| BBS1 | 0.224 | 0.030 | 0.047 | 0.454 | 0.22 | 0.94 | 0.033 | 0.032 |
| RBM15 | 0.324 | 0.030 | 0.044 | 2.392 | 1.08 | 5.32 | 0.033 | 0.034 |
| NPFF | 0.326 | 0.031 | 0.045 | 0.378 | 0.17 | 0.83 | 0.016 | 0.017 |
| AKR7A2 | 0.455 | 0.032 | 0.024 | 0.546 | 0.35 | 0.85 | 0.008 | 0.008 |
| STRA13 | 0.501 | 0.033 | 0.024 | 0.478 | 0.28 | 0.83 | 0.009 | 0.008 |
| SLC25A42 | 0.627 | 0.033 | 0.009 | 0.380 | 0.21 | 0.69 | 0.002 | 0.001 |
| CCP110 | 0.620 | 0.034 | 0.029 | 2.453 | 1.21 | 4.99 | 0.013 | 0.014 |
| ZNF862 | 0.386 | 0.034 | 0.049 | 0.535 | 0.32 | 0.89 | 0.017 | 0.017 |
| RGS14 | 0.359 | 0.034 | 0.049 | 0.537 | 0.31 | 0.92 | 0.024 | 0.024 |
| MFAP1 | 0.466 | 0.035 | 0.032 | 2.602 | 1.21 | 5.58 | 0.014 | 0.014 |
| ZNF35 | 0.281 | 0.035 | 0.047 | 2.135 | 1.14 | 3.99 | 0.018 | 0.021 |
| SQSTM1 | 0.389 | 0.035 | 0.031 | 2.594 | 1.23 | 5.49 | 0.013 | 0.013 |
| ABL1 | 0.998 | 0.036 | 0.002 | 3.382 | 1.63 | 7.02 | 0.001 | 0.001 |
| ERRFI1 | 0.249 | 0.036 | 0.039 | 1.555 | 1.05 | 2.29 | 0.026 | 0.024 |
| AUH | 0.293 | 0.036 | 0.047 | 0.570 | 0.35 | 0.92 | 0.022 | 0.021 |
| CDK5 | 0.395 | 0.037 | 0.033 | 0.501 | 0.29 | 0.87 | 0.014 | 0.014 |
| FBF1 | 0.992 | 0.038 | 0.012 | 0.229 | 0.09 | 0.58 | 0.002 | 0.002 |
| SLC2A13 | 0.367 | 0.038 | 0.046 | 0.446 | 0.21 | 0.94 | 0.034 | 0.030 |
| MOSPD3 | 0.587 | 0.039 | 0.027 | 0.409 | 0.21 | 0.80 | 0.008 | 0.009 |
| STX8 | 0.390 | 0.039 | 0.048 | 0.580 | 0.38 | 0.89 | 0.013 | 0.013 |
| GALT | 0.503 | 0.039 | 0.033 | 0.506 | 0.30 | 0.86 | 0.012 | 0.012 |
| MGAT2 | 0.402 | 0.040 | 0.044 | 2.313 | 1.12 | 4.76 | 0.023 | 0.022 |
| NR2E3 | 0.435 | 0.040 | 0.042 | 0.433 | 0.22 | 0.85 | 0.016 | 0.014 |
| CLNS1A | 0.510 | 0.040 | 0.024 | 0.514 | 0.32 | 0.83 | 0.006 | 0.007 |
| ZSCAN22 | 0.498 | 0.041 | 0.046 | 3.886 | 1.24 | 12.19 | 0.020 | 0.022 |
| STARD8 | 0.367 | 0.042 | 0.047 | 2.024 | 1.12 | 3.65 | 0.019 | 0.020 |
| ZNF248 | 0.635 | 0.042 | 0.013 | 0.496 | 0.30 | 0.81 | 0.005 | 0.004 |
| THBS3 | 0.419 | 0.042 | 0.046 | 0.402 | 0.19 | 0.86 | 0.019 | 0.019 |
| DUSP22 | 0.397 | 0.043 | 0.049 | 0.545 | 0.33 | 0.90 | 0.019 | 0.018 |
| DESI2 | 0.600 | 0.044 | 0.034 | 2.714 | 1.21 | 6.07 | 0.015 | 0.015 |
| PLXNC1 | 0.481 | 0.044 | 0.036 | 0.548 | 0.33 | 0.91 | 0.019 | 0.020 |
| MCFD2 | 0.609 | 0.045 | 0.026 | 2.229 | 1.25 | 3.99 | 0.007 | 0.007 |
| INTS7 | 0.886 | 0.046 | 0.005 | 0.399 | 0.22 | 0.71 | 0.002 | 0.001 |
| MPP6 | 0.501 | 0.046 | 0.036 | 2.568 | 1.20 | 5.51 | 0.016 | 0.018 |
| TRAPPC6A | 0.609 | 0.049 | 0.021 | 0.391 | 0.20 | 0.76 | 0.005 | 0.006 |
| RBM3 | 0.553 | 0.050 | 0.047 | 0.476 | 0.26 | 0.88 | 0.017 | 0.017 |

TABLE 2

Nanostring Single Arm and Interaction Association with 37 genes

| | Sipuleucel-T arm OS association | | | | | Combined Sip-T + Control arm OS association | | |
|---|---|---|---|---|---|---|---|---|
| Gene | Expression Hazard Ratio | Expression Hazard Ratio (Lower) | Expression Hazard Ratio (Upper) | Expression P value | Irt. p p value | Expression p value | Ineraction p value | Irt. p |
| CUL9 | 0.518 | 0.362 | 0.741 | 0.000 | 0.000 | 0.497 | 0.017 | 0.002 |
| ITGAL | 0.520 | 0.352 | 0.767 | 0.001 | 0.001 | 0.138 | 0.002 | 0.002 |
| ARHGDIB | 0.354 | 0.194 | 0.645 | 0.001 | 0.001 | 0.079 | 0.001 | 0.001 |
| CASP1 | 0.582 | 0.408 | 0.828 | 0.003 | 0.002 | 0.009 | 0.000 | 0.000 |
| JAK1 | 0.334 | 0.163 | 0.686 | 0.003 | 0.003 | 0.351 | 0.016 | 0.011 |
| IL2RG | 0.571 | 0.392 | 0.831 | 0.003 | 0.003 | 0.427 | 0.027 | 0.011 |
| NCAM1 | 0.656 | 0.488 | 0.881 | 0.005 | 0.005 | 0.504 | 0.031 | 0.019 |
| C1QA | 0.728 | 0.585 | 0.905 | 0.004 | 0.005 | 0.016 | 0.000 | 0.002 |
| STAT2 | 0.650 | 0.476 | 0.886 | 0.006 | 0.006 | 0.001 | 0.000 | 0.000 |
| ATM | 0.661 | 0.490 | 0.893 | 0.007 | 0.009 | 0.732 | 0.050 | 0.038 |
| IKBKE | 0.600 | 0.408 | 0.882 | 0.009 | 0.009 | 0.237 | 0.022 | 0.025 |
| BATF3 | 0.690 | 0.524 | 0.907 | 0.008 | 0.010 | 0.279 | 0.014 | 0.018 |
| CASP2 | 0.503 | 0.298 | 0.851 | 0.010 | 0.010 | 0.054 | 0.005 | 0.009 |
| IL18 | 0.702 | 0.531 | 0.927 | 0.013 | 0.012 | 0.014 | 0.000 | 0.002 |
| ITGB2 | 0.598 | 0.401 | 0.891 | 0.012 | 0.012 | 0.111 | 0.006 | 0.017 |
| IRAK4 | 0.564 | 0.363 | 0.878 | 0.011 | 0.012 | 0.055 | 0.004 | 0.009 |

TABLE 2-continued

Nanostring Single Arm and Interaction Association with 37 genes

| | Sipuleucel-T arm OS association | | | | | Combined Sip-T + Control arm OS association | | |
|---|---|---|---|---|---|---|---|---|
| Gene | Expression Hazard Ratio | Expression Hazard Ratio (Lower) | Expression Hazard Ratio (Upper) | Expression P value | Irt. p value | Expression p value | Ineraction p value | Irt. p |
| PDGFB | 0.699 | 0.530 | 0.921 | 0.011 | 0.012 | 0.346 | 0.031 | 0.042 |
| CCL23 | 0.759 | 0.610 | 0.944 | 0.013 | 0.014 | 0.199 | 0.019 | 0.033 |
| CCL20 | 0.845 | 0.737 | 0.968 | 0.015 | 0.015 | 0.010 | 0.001 | 0.002 |
| NFKBIZ | 0.704 | 0.530 | 0.937 | 0.016 | 0.016 | 0.029 | 0.001 | 0.006 |
| TAPBP | 0.391 | 0.181 | 0.845 | 0.017 | 0.017 | 0.004 | 0.000 | 0.002 |
| LTB4R | 0.562 | 0.343 | 0.921 | 0.022 | 0.020 | 0.276 | 0.024 | 0.042 |
| IL1A | 0.823 | 0.697 | 0.972 | 0.022 | 0.021 | 0.026 | 0.002 | 0.006 |
| IFNG | 0.824 | 0.694 | 0.978 | 0.027 | 0.022 | 0.001 | 0.000 | 0.001 |
| PTGS2 | 0.809 | 0.675 | 0.969 | 0.021 | 0.022 | 0.001 | 0.000 | 0.000 |
| FCGR1A | 0.756 | 0.597 | 0.958 | 0.021 | 0.025 | 0.155 | 0.017 | 0.045 |
| PDGFRB | 0.748 | 0.583 | 0.960 | 0.022 | 0.027 | 0.164 | 0.015 | 0.038 |
| TNF | 0.743 | 0.569 | 0.969 | 0.029 | 0.028 | 0.043 | 0.003 | 0.012 |
| CMKLR1 | 0.752 | 0.579 | 0.977 | 0.033 | 0.034 | 0.024 | 0.002 | 0.009 |
| IL10RA | 0.597 | 0.371 | 0.961 | 0.034 | 0.034 | 0.027 | 0.003 | 0.012 |
| CYBB | 0.716 | 0.527 | 0.972 | 0.032 | 0.035 | 0.071 | 0.008 | 0.025 |
| CCL4 | 0.859 | 0.746 | 0.990 | 0.035 | 0.037 | 0.007 | 0.001 | 0.003 |
| CD55 | 0.729 | 0.539 | 0.987 | 0.041 | 0.040 | 0.222 | 0.018 | 0.049 |
| PRF1 | 0.773 | 0.601 | 0.995 | 0.045 | 0.042 | 0.017 | 0.003 | 0.010 |
| CCL3 | 0.857 | 0.738 | 0.996 | 0.044 | 0.046 | 0.004 | 0.001 | 0.002 |
| ITGAX | 0.713 | 0.514 | 0.991 | 0.044 | 0.046 | 0.075 | 0.007 | 0.024 |
| PTGER4 | 0.652 | 0.426 | 0.998 | 0.049 | 0.049 | 0.003 | 0.001 | 0.004 |

Similar numbers of samples were profiled using the Nanostring and Affymetrix data analysis. For Nanostring, 251 total subjects were analyzed (sipuleucel-T n=169; control n=82) and for Affymetrix data, 255 total subjects (sipuleucel-T n=172; control n=83) were analyzed. As shown in FIG. 1, the p-value distributions of the association with overall survival using Equations (1) and (2), show the extent of signal of NanoString data.

As shown in FIG. 2, the p-value distributions of the association with overall survival using Equations (1) and (2), show the extent of signal of Affymetrix data. A peak towards the lower p-value distribution in FIG. 2 indicates that more genes are associated with overall survival, with p≤0.05, than what is expected by chance.

To identity candidate genes associated with overall survival, the genes that were significant (p≤0.05) were identified, in terms of the following: (1) treatment:gene-expression interaction in the combined arms analysis (Equation (1)), which indicates that the association between gene-expression and overall survival is different between the two arms; (2) likelihood ratio test comparing the full-model (Equation (1)) to the base model (Equation (3)) in the combined arm; (3) gene expression association in the sipuleucel-T arm (Equation (2)), which indicates that the gene-expression is associated with overall survival in the sipuleucel-T arm; and (4) likelihood ratio test comparing the full-model (Equation (2)) to the base model (Equation (3)) in the sipuleucel-T arm.

As provided by the Nanostring data, ninety three (93) genes were significant when considering criteria 1 and 2 above (combined arm), and eighty one (81) genes were significant when considering criteria 3 and 4 (sipuleucel-T arm). Thirty seven (37) genes are common between the combined arm analysis and sipuleucel-T arm analyses.

As provided by the Affymetrix data, two hundred twenty-four (224) genes were significant when considering criteria 1 and 2 (combined arm), and seven hundred forty-six (746) genes were significant when considering criteria 3 and 4 (sipuleucel-T arm). One hundred fifty-one (151) genes were common between the combined arm analyses and sipuleucel-T arm analyses.

Permutation based assessment of false discovery rates in association of gene expression with overall survival One thousand random permutations were used to assess the False Discovery Rate (FDR) of significant genes at p-value threshold of 0.05 (i.e., the number of genes that seem to be associated with overall survival by chance). The frequency distribution of the number of genes significantly associated with overall survival with a p-value threshold of 0.05 was determined from the Nanostring data. As shown in FIG. 3, a histogram of the number of genes that were significant (using the combined set of 4 criteria) in each of one thousand permutations was plotted. Distribution of the number of genes from Nanostring data indicates that there is 0.1% chance that the 37 candidate genes could have appeared significant by chance. The first two vertical lines from the left represent the 50$^{th}$ and 95$^{th}$ percentiles respectively. The last line indicates the 37 gene candidates that meet the criteria with real data.

As shown in FIG. 4, distribution of the number of genes from Affymetrix data indicates a probability of 0.04 that 151 candidate genes could have appeared significant by chance. The first line form the left represents the 95$^{th}$ percentile. The second line from the left indicates the 151 gene candidates that were found in the real data.

Interpretation of signaling and functional pathways in genes associated with overall survival Using Ingenuity Pathway Analysis (IPA) as found at http://www.ingenuity.com/products/pathways_analysis.html, the functional pathways that may be associated with the candidate genes were explored. Nanostring gene candidates (37 genes) are predicted to be involved in TNF and IFNγ production and signaling.

Functional interpretation of 151 Affymetrix gene candidates using IPA showed no significant enrichment of pathways. These genes were evaluated using external GEO (Gene expression Omnibus database) datasets for activation and maturation pathways of T-cells, B-cells, dendritic cells, monocytes, macrophages, natural killer cells. Genes within four pathways were associated with overall survival (unadjusted $p \leq 0.05$). The four pathways are listed as follows: (i) NF-KB Signaling; (ii) Role of RIG1-like receptors in antiviral innate immunity; (iii) Clathrin-mediated Endocytosis signaling; and (iv) IL-3 signaling.

Overlap Between Nanostring and Affymetrix Gene Candidates

Although there were 412 genes that were common between Affymetrix and Nanostring (after filtering for low-variation probes in the Affymetrix platform), surprisingly, there was no overlap between the 37 Nanostring candidate genes and 151 Affymetrix candidate genes from the two platforms.

Selection of Predictive Gene Markers for qPCR Confirmation

To evaluate which genes are predictive gene expression markers of sipuleucel-T, gene candidates from the Nanostring data and Affymetrix data were selected for qPCR confirmation. All 37 Nanostring gene candidates from the NanoString platform were selected for qPCR confirmation. The top 50 genes from the 151 Affymetrix candidates were prioritized based on increasing values of the treatment:gene-expression interaction (Equation (2)). In addition to the candidate genes from NanoString and Affymetrix platforms, 67 immunological relevant genes involved in immune biology that could be associated with the mechanism of action of sipuleucel-T (e.g., genes associated with activation or amounts of APC, T cell, B cell, natural killer cells in PBMCs) were also included. Thus, qPCR validation was conducted on 3 panels, having all three groups of genes—Nanostring candidates, Affymetrix candidates, and genes with immuno-biological rationale.

The three qPCR gene panels are given below:

qPCR Panel 1

| Nanostring 25 Genes | STAT2 | CASP1 | PTGS2 | IFNG | TAPBP | IL18 | C1QA | CCL3 | CCL20 | CCL4 |
|---|---|---|---|---|---|---|---|---|---|---|
| | PTGER4 | ARHGDIB | NFKBIZ | IL1A | ITGAL | CMKLR1 | PRF1 | IL10RA | TNF | IRAK4 |
| | CASP2 | ITGB2 | ITGAX | CYBB | BATF3 | | | | | |
| Affymetrix 16 Genes | ABCC5 | CEP57L1 | HEXDC | NIT2 | NR1D2 | NSRP1 | NTSR1 | PEX13 | SLC25A32 | SLK |
| | SNTB1 | SYNGR3 | TILL5 | UBXN 8 | VPS53 | DSEL | | | | |
| Biological Rationale 17 Genes | CD27 | CD274 | CD28 | CD4 | CD40 | CD80 | CD8A | CSF2RA | CSF2RB | CTLA4 |
| | FOXP3 | HLA-DRA | HLA-DRB3 | ICAM1 | IDO1 | IL2RA | PDCD1 | | | |

Primers for the gene DSEL (Affymetrix gene candidate) were not available from Bio-Rad and therefore, the gene DSEL was not tested.

qPCR Panel 2

| Affymetrix 14 Genes Biological Rationale 43 Genes | BBS9 | AURKC | CYTH2 | ABL1 | ZNF268 | SYTL1 | MUM1 | SLC25A42 | INTS7 | FBF1 |
|---|---|---|---|---|---|---|---|---|---|---|
| | ASB9 | SFXN2 | RAB3GAP1 | ROBO3 | | | | | | |
| | ABL2 | SEMA4D | TIMP1 | CDKN1A | TERF2IP | RIOK3 | GABARAPL2 | CRISP2 | SNCA | IFI27 |
| | MMP8 | GYPA | STOM | TMCC2 | CD33 | ARG1 | NOS2 | CD3D | CXCR4 | TNFRSF4 |
| | TNFRSF9 | CD40LG | CD19 | SDC1 | CD38 | IGKC | KLRK1 | FCGR2A | FCGR1A | CD83 |
| | CD14 | IL6 | IL2 | CCL5 | IL10 | GZMB | CXCL10 | HAVCR2 | CD274 | NFKB1 |
| | NFKB2 | ZAP70 | LAG3 | | | | | | | |

The following candidate genes were selected based on prostate cancer prognostic genes suggested in Ross et al.: ABL12, SEMA41D, TIMP1, CDKN1A, (Ross et al., *Lancet Oncology*, 2012 13: 1105-1113). The following candidate genes were selected based on prostate cancer prognostic genes suggested in Olmos et al.: TERF2IP, RIOK3, GABARAPL2, CRISP2, SNCA, IF127, MMP8, GYPA, STOM, TMCC2 (Olmos et al., *Lancet Oncology*, 2012 13: 1114-1124).

qPCR Panel 3

| Nanostring 16 Genes | CUL9 | JAK1 | IL2RG | NCAM1 | ATM | IKBKE | PDGFB | CCL23 | CFH | LTB4R |
|---|---|---|---|---|---|---|---|---|---|---|
| | CISH | PDGFRB | CD55 | PRDM1 | CXCR6 | ENTPD1 | | | | |
| Affymetrix 20 Genes | POLH | ZNF248 | B3GALTL | TMEM119 | VEZT | HEMK1 | TRAPPC6A | COMMD6 | CLNS1A | CHI3L2 |
| | MCFD2 | IFT27 | AKR7A2 | MOSIPD3 | STRA13 | ACOT13 | MLLT6 | ABCA7 | CEP41 | TRIM16 |
| Biological Rationale 21 Genes | IL3 | IL4 | IL5 | IL13 | STAT1 | STAT3 | STAT4 | STAT6 | TNFRSF18 | TBX21 |
| | CCR7 | FCGR3A | IL7R | MS4A1 | BCL2L11 | HIF1A | NCR1 | ITGAM | FUT4 | IL3RA |
| | ARG2 | | | | | | | | | |

Example 3: PrimePCR™ Panels 1, 2, and 3 Using Halabi 2003

This example discloses gene expression profiling data identifying genes in qPCR Panel 1 whose expression in PBMC samples from prostate cancer patients is significantly associated with overall survival after treatment with sipuleucel-T. PBMC samples from 4 IMPACT patients were used for this evaluation. Each PrimePCR™ plate (Bio-Rad) contained 64 analytes, including 57 candidate genes set forth as qPCR Panel 1 and seven control analytes. Three samples were run in duplicate in a single 384 well plate. The control analytes included the following (i) platform controls of gDNA, PCR, and RT; and (ii) reference genes of GUSB, GAPDH, RPL19, HPRT1. qPCR runs were perform on a Bio-Rad CFX384 touch real-time instrument coupled with an automatic plate feeder using PrimePCR™ custom 384 plates. Data was subject to quality control using the platform controls.

Evaluation of Candidate Predictive Genes

Results of association of the gene expression profiles with overall survival are provided below:

TABLE 3

Association of gene expression variables with OS in the sipuleucel-T arm:

| GENE | GENE HR | GENE HR LOWER 95% CI | GENE HR HIGHER 95% CI | P-VALUE | LIKELIHOOD RATIO P-VALUE (FULL TO BASE |
|---|---|---|---|---|---|
| ABCC5 | 0.832 | 0.677 | 1.021 | 0.078 | 0.072 |
| ARHGDIB | 0.678 | 0.437 | 1.051 | 0.083 | 0.087 |
| BATF3 | 0.843 | 0.685 | 1.039 | 0.109 | 0.118 |
| C1QA | 0.944 | 0.755 | 1.180 | 0.612 | 0.612 |
| CASP1 | 0.814 | 0.582 | 1.139 | 0.230 | 0.231 |
| CASP2 | 0.862 | 0.575 | 1.293 | 0.473 | 0.471 |
| CCL20 | 0.998 | 0.891 | 1.117 | 0.967 | 0.967 |
| CCL3 | 0.989 | 0.876 | 1.118 | 0.862 | 0.862 |
| CCL4 | 0.988 | 0.876 | 1.115 | 0.846 | 0.846 |
| CD27 | 0.911 | 0.730 | 1.136 | 0.407 | 0.404 |
| CD274 | 1.038 | 0.871 | 1.238 | 0.678 | 0.678 |
| CD28 | 0.934 | 0.733 | 1.190 | 0.579 | 0.588 |
| CD4 | 0.784 | 0.559 | 1.100 | 0.159 | 0.167 |
| CD40 | 0.994 | 0.805 | 1.228 | 0.957 | 0.957 |
| CD80 | 1.130 | 0.929 | 1.374 | 0.221 | 0.215 |
| CD8A | 1.190 | 0.975 | 1.451 | 0.087 | 0.086 |
| CD8B | 1.076 | 0.875 | 1.324 | 0.486 | 0.484 |
| CEP57L1 | 1.016 | 0.769 | 1.342 | 0.910 | 0.910 |
| CMKLR1 | 0.900 | 0.710 | 1.140 | 0.382 | 0.385 |
| CSF2RA | 0.997 | 0.653 | 1.523 | 0.989 | 0.989 |
| CSF2RB | 0.959 | 0.761 | 1.208 | 0.722 | 0.728 |
| CTLA4 | 1.015 | 0.789 | 1.306 | 0.906 | 0.906 |
| CYBB | 0.799 | 0.582 | 1.098 | 0.167 | 0.170 |
| DSEL | 0.993 | 0.860 | 1.146 | 0.921 | 0.921 |
| FOXP3 | 1.155 | 0.929 | 1.437 | 0.195 | 0.186 |
| HEXDC | 0.893 | 0.745 | 1.069 | 0.218 | 0.221 |
| HLA-DRA | 1.225 | 1.029 | 1.457 | 0.022 | 0.002 |
| ICAM1 | 0.946 | 0.686 | 1.304 | 0.732 | 0.733 |
| IDO1 | 1.078 | 0.969 | 1.199 | 0.167 | 0.166 |
| IFNG | 1.004 | 0.892 | 1.129 | 0.953 | 0.953 |
| IL10RA | 0.727 | 0.538 | 0.983 | 0.038 | 0.058 |
| IL18 | 0.885 | 0.731 | 1.072 | 0.211 | 0.215 |
| IL1A | 0.985 | 0.870 | 1.114 | 0.808 | 0.808 |
| IL2RA | 1.131 | 0.926 | 1.380 | 0.228 | 0.229 |
| IRAK4 | 0.857 | 0.573 | 1.280 | 0.451 | 0.454 |
| ITGAL | 0.881 | 0.677 | 1.146 | 0.346 | 0.348 |
| ITGAX | 0.868 | 0.591 | 1.274 | 0.469 | 0.474 |
| ITGB2 | 0.832 | 0.596 | 1.164 | 0.283 | 0.290 |
| NFKBIZ | 0.896 | 0.731 | 1.098 | 0.290 | 0.291 |
| NIT2 | 0.817 | 0.510 | 1.308 | 0.400 | 0.404 |
| NR1D2 | 1.064 | 0.658 | 1.720 | 0.800 | 0.800 |
| NSRP1 | 1.754 | 1.034 | 2.973 | 0.037 | 0.037 |

TABLE 3-continued

Association of gene expression variables with OS in the sipuleucel-T arm:

| GENE | GENE HR | GENE HR LOWER 95% CI | GENE HR HIGHER 95% CI | P-VALUE | LIKELIHOOD RATIO P-VALUE (FULL TO BASE |
|---|---|---|---|---|---|
| NTSR1 | 1.160 | 1.004 | 1.340 | 0.044 | 0.036 |
| PDCD1 | 1.055 | 0.892 | 1.247 | 0.532 | 0.529 |
| PEX13 | 0.973 | 0.853 | 1.111 | 0.689 | 0.688 |
| PRF1 | 1.117 | 0.901 | 1.384 | 0.312 | 0.315 |
| PTGER4 | 1.019 | 0.760 | 1.368 | 0.899 | 0.898 |
| PTGS2 | 0.968 | 0.852 | 1.100 | 0.623 | 0.624 |
| SLC25A32 | 1.480 | 0.937 | 2.338 | 0.093 | 0.093 |
| SLK | 1.430 | 0.806 | 2.537 | 0.221 | 0.219 |
| SNTB1 | 0.739 | 0.563 | 0.971 | 0.030 | 0.030 |
| STAT2 | 0.914 | 0.685 | 1.221 | 0.544 | 0.543 |
| SYNGR3 | 1.383 | 1.090 | 1.754 | 0.008 | 0.007 |
| TAPBP | 1.160 | 0.628 | 2.144 | 0.636 | 0.635 |
| TNF | 0.923 | 0.771 | 1.104 | 0.380 | 0.381 |
| TTLL5 | 0.709 | 0.516 | 0.974 | 0.034 | 0.037 |
| VPS53 | 1.083 | 0.687 | 1.709 | 0.731 | 0.731 |

TABLE 4

Association of gene expression variables with OS in the control arm.

| GENE | GENE HR | GENE HR LOWER 95% CI | GENE HR HIGHER 95% CI | P-VALUE | LIKELIHOOD RATIO P-VALUE (FULL TO BASE MODEL) |
|---|---|---|---|---|---|
| ABCC5 | 1.129 | 0.849 | 1.502 | 0.404 | 0.404 |
| ARHGDIB | 1.393 | 0.727 | 2.669 | 0.317 | 0.313 |
| BATF3 | 0.981 | 0.738 | 1.303 | 0.892 | 0.893 |
| C1QA | 1.187 | 0.867 | 1.626 | 0.285 | 0.282 |
| CASP1 | 1.390 | 0.879 | 2.199 | 0.159 | 0.145 |
| CASP2 | 1.202 | 0.689 | 2.096 | 0.517 | 0.520 |
| CCL20 | 1.034 | 0.877 | 1.218 | 0.693 | 0.692 |
| CCL3 | 1.089 | 0.926 | 1.282 | 0.304 | 0.297 |
| CCL4 | 1.104 | 0.940 | 1.297 | 0.228 | 0.218 |
| CD27 | 0.860 | 0.621 | 1.192 | 0.366 | 0.365 |
| CD274 | 0.975 | 0.802 | 1.187 | 0.803 | 0.803 |
| CD28 | 1.126 | 0.799 | 1.587 | 0.498 | 0.496 |
| CD4 | 0.770 | 0.414 | 1.432 | 0.408 | 0.412 |
| CD40 | 0.951 | 0.668 | 1.354 | 0.780 | 0.780 |
| CD80 | 1.081 | 0.826 | 1.413 | 0.571 | 0.570 |
| CD8A | 1.164 | 0.871 | 1.555 | 0.305 | 0.307 |
| CD8B | 1.031 | 0.776 | 1.369 | 0.834 | 0.834 |
| CEP57L1 | 1.257 | 0.903 | 1.750 | 0.175 | 0.176 |
| CMKLR1 | 1.191 | 0.924 | 1.536 | 0.177 | 0.173 |
| CSF2RA | 0.794 | 0.436 | 1.446 | 0.451 | 0.455 |
| CSF2RB | 1.034 | 0.765 | 1.397 | 0.829 | 0.827 |
| CTLA4 | 0.951 | 0.677 | 1.336 | 0.772 | 0.773 |
| CYBB | 1.081 | 0.703 | 1.661 | 0.723 | 0.722 |
| DSEL | 1.039 | 0.888 | 1.214 | 0.635 | 0.631 |
| FOXP3 | 0.899 | 0.664 | 1.218 | 0.492 | 0.493 |
| HEXDC | 1.050 | 0.831 | 1.326 | 0.682 | 0.681 |
| HLA-DRA | 0.989 | 0.555 | 1.760 | 0.969 | 0.969 |
| ICAM1 | 0.973 | 0.645 | 1.467 | 0.895 | 0.895 |
| IDO1 | 1.059 | 0.919 | 1.219 | 0.428 | 0.426 |
| IFNG | 1.185 | 0.986 | 1.424 | 0.071 | 0.062 |
| IL10RA | 0.984 | 0.544 | 1.781 | 0.958 | 0.958 |
| IL18 | 1.113 | 0.872 | 1.422 | 0.390 | 0.387 |
| IL1A | 1.008 | 0.825 | 1.233 | 0.935 | 0.935 |
| IL2RA | 1.167 | 0.837 | 1.626 | 0.362 | 0.366 |
| IRAK4 | 1.333 | 0.822 | 2.161 | 0.244 | 0.240 |
| ITGAL | 0.961 | 0.693 | 1.334 | 0.814 | 0.815 |
| ITGAX | 0.973 | 0.484 | 1.955 | 0.938 | 0.938 |
| ITGB2 | 1.044 | 0.631 | 1.729 | 0.866 | 0.866 |
| NFKBIZ | 1.001 | 0.761 | 1.317 | 0.992 | 0.992 |
| NIT2 | 1.173 | 0.710 | 1.937 | 0.533 | 0.531 |
| NR1D2 | 0.741 | 0.345 | 1.592 | 0.442 | 0.440 |

TABLE 4-continued

Association of gene expression variables with OS in the control arm.

| GENE | GENE HR | GENE HR LOWER 95% CI | GENE HR HIGHER 95% CI | P-VALUE | LIKELIHOOD RATIO P-VALUE (FULL TO BASE MODEL) |
|---|---|---|---|---|---|
| NSRP1 | 0.704 | 0.295 | 1.680 | 0.429 | 0.431 |
| NTSR1 | 0.899 | 0.786 | 1.027 | 0.117 | 0.130 |
| PDCD1 | 0.889 | 0.713 | 1.109 | 0.297 | 0.301 |
| PEX13 | 0.894 | 0.554 | 1.443 | 0.647 | 0.646 |
| PRF1 | 1.356 | 1.009 | 1.820 | 0.043 | 0.042 |
| PTGER4 | 1.438 | 0.890 | 2.324 | 0.138 | 0.132 |
| PTGS2 | 1.139 | 0.937 | 1.385 | 0.190 | 0.177 |
| SLC25A32 | 0.925 | 0.473 | 1.810 | 0.821 | 0.821 |
| SLK | 0.788 | 0.346 | 1.793 | 0.570 | 0.570 |
| SNTB1 | 1.208 | 0.832 | 1.754 | 0.320 | 0.319 |
| STAT2 | 1.390 | 0.936 | 2.066 | 0.103 | 0.095 |
| SYNGR3 | 0.796 | 0.589 | 1.075 | 0.137 | 0.135 |
| TAPBP | 1.229 | 0.596 | 2.537 | 0.577 | 0.568 |
| TNF | 1.080 | 0.845 | 1.382 | 0.539 | 0.536 |
| TTLL5 | 0.885 | 0.560 | 1.399 | 0.601 | 0.602 |
| VPS53 | 1.064 | 0.621 | 1.822 | 0.821 | 0.821 |

TABLE 5

Association of gene expression variables with overall survival in the combined sipuleucel-T + control arms.

| GENE | TREATMENT:GENE INTERACTION P-VALUE | LIKELIHOOD RATIO P-VALUE (FULL TO BASE MODEL) |
|---|---|---|
| ABCC5 | 0.109 | 0.005 |
| ARHGDIB | 0.087 | 0.005 |
| BATF3 | 0.304 | 0.007 |
| C1QA | 0.260 | 0.015 |
| CASP1 | 0.052 | 0.004 |
| CASP2 | 0.378 | 0.018 |
| CCL20 | 0.456 | 0.021 |
| CCL3 | 0.177 | 0.010 |
| CCL4 | 0.166 | 0.010 |
| CD27 | 0.830 | 0.016 |
| CD274 | 0.774 | 0.026 |
| CD28 | 0.447 | 0.021 |
| CD4 | 0.987 | 0.008 |
| CD40 | 0.627 | 0.024 |
| CD80 | 0.738 | 0.013 |
| CD8A | 0.822 | 0.003 |
| CD8B | 0.712 | 0.019 |
| CEP57L1 | 0.474 | 0.016 |
| CMKLR1 | 0.247 | 0.015 |
| CSF2RA | 0.798 | 0.024 |
| CSF2RB | 0.746 | 0.024 |
| CTLA4 | 0.917 | 0.027 |
| CYBB | 0.296 | 0.009 |
| DSEL | 0.810 | 0.026 |
| FOXP3 | 0.182 | 0.009 |
| HEXDC | 0.393 | 0.016 |
| HLA-DRA | 0.356 | 0.000 |
| ICAM1 | 0.669 | 0.023 |
| IDO1 | 0.969 | 0.008 |
| IFNG | 0.106 | 0.005 |
| IL10RA | 0.243 | 0.004 |
| IL18 | 0.113 | 0.008 |
| IL1A | 0.638 | 0.024 |
| IL2RA | 0.950 | 0.010 |
| IRAK4 | 0.311 | 0.017 |
| ITGAL | 0.758 | 0.017 |
| ITGAX | 0.559 | 0.018 |
| ITGB2 | 0.549 | 0.016 |
| NFKBIZ | 0.320 | 0.012 |
| NIT2 | 0.481 | 0.020 |
| NR1D2 | 0.359 | 0.018 |
| NSRP1 | 0.055 | 0.002 |
| NTSR1 | 0.013 | 0.001 |
| PDCD1 | 0.352 | 0.018 |
| PEX13 | 0.989 | 0.024 |
| PRF1 | 0.425 | 0.003 |
| PTGER4 | 0.172 | 0.008 |
| PTGS2 | 0.082 | 0.006 |
| SLC25A32 | 0.245 | 0.007 |
| SLK | 0.179 | 0.010 |
| SNTB1 | 0.049 | 0.002 |
| STAT2 | 0.143 | 0.010 |
| SYNGR3 | 0.004 | <0.001 |
| TAPBP | 0.902 | 0.020 |
| TNF | 0.224 | 0.013 |
| TTLL5 | 0.460 | 0.004 |
| VPS53 | 0.812 | 0.025 |

Statistical Analysis: Association of Gene Expression Profiles with Overall Survival Using Cox Models Association of gene expression levels with overall survival was performed using a multivariate Cox proportional hazards regression model, where overall survival was fit to the gene expression variable along with prognostic factors described by Halabi et. al (Halabi, S., et al., *J Clin Oncol*, 2003 21(7):1232-7)), viz. PSA (log), LDH (log), Alkaline phosphatase (log), Hemoglobin, Total Gleason score ($\leq 7$, $>7$), and ECOG status (0, 1). OS associations were only reported for the treatment:gene expression interaction (Equation (4)), or the gene expression variable (Equation (5)) using Wald's test. A likelihood ratio test was also performed to determine the improvement of fit to OS due to gene-expression variable by comparing the full models (as given in Equations (4) and (5)) to the base model (Cox model using only the prognostic variables from Halabi nomogram, Equation (6). No adjustments of the p-values were made for multiple testing. Hazard ratios (HRs) were reported for single arm analyses.

Association of gene expression with overall survival was performed using the following models:

Combined analysis of sipuleucel-T and control arms: In the survival fit, along with the prognostic factors, an interaction factor between treatment arm (sipuleucel-T and control) and gene expression measures was included. The OS model used was:

Survival~PSA+LDH+Alkaline phosphatase+Hemoglobin+Total Gleason score+ECOG status+
GENE EXPRESSION*TREATMENT ARM    Equation (4)

Analysis of sipuleucel-T arm: In the survival fit, along with the prognostic factors gene expression measures from sipuleucel-T arm only were included. The OS model used was:

Survival~PSA+LDH+Alkaline phosphatase+Hemoglobin+Total Gleason score+ECOG status+
GENE EXPRESSION    Equation (5)

Base model applied as comparison model to both sipuleucel-T only and sipuleucel-T+control arms (only used for likelihood ratio testing): with Halabi 2003 prognostic variables only Survival~PSA+LDH+Alkaline phosphatase+Hemoglobin+Total Gleason score+ECOG status    Equation (6)

Candidates were considered to be confirmed if they were associated in the sipuleucel-T arm with Wald's test $p \leq 0.05$ and likelihood ratio test p≤0.05 (comparing models 5 and 6). Candidates were also considered to be confirmed if they had significant treatment:gene interaction (p≤0.05, Equation (5)), and were significant in likelihood ratio test with p≤0.05 in the combined arm analysis (comparing models 4 and 6). Two genes from Panel 1 were obtained with these thresholds: SNTB1, and SYNGR3. Two genes from Panel 2 were obtained with these thresholds: AURKC and ZNF268. One gene from Panel 3 was obtained with these thresholds: CHI3L2. FIGS. 5A-5E show the overall survival plots for the five gene candidates with significant overall association in qPCR Panels 1, 2, and 3. Specifically, the p value for the candidate genes were as follows: SNTB1 (p=0.0482), SYNGR3 (p=0.0207), AURKC (p=0.0303), ZNF268 (p=0.0263), CHI132 (p=0.0246). As shown in the overall survival plots of FIGS. 5A-5E, upregulation of SNTB1 and CHI132 is associated with better overall survival and downregulation of SYNGR3, AURKC, and ZNF268 is associated with better overall survival.

A composite expression was strongly associated with overall survival in IMPACT. The composite gene expression score linearly combines the log expressions of the genes, keeping in consideration the direction association as given by the hazard ratios.

Composite Gene Expression Score: Log Expression (SNTB1)−Log Expression (SYNGR3) Log Expression (AURKC)−Log Expression (ZNF268)+Log Expression (CHI3L2)  Equation (7)

As shown in FIG. 6, the Kaplan-Meier method was used to show survival of the patient groups described above. The subjects within the top tertile were significantly different from the control arm subjects in terms of overall survival (p≤0.05). More specifically, the plot shows that patients within the highest tertile of composite expression score in the sipuleucel-T arm were more likely to survive relative to a control group. Subjects in the sipuleucel-T arm were segmented according to tertiles of the composite expression score. For this association, the following Cox model was used:

Survival~PSA+LDH+Alkaline phosphatase+Hemoglobin+Total Gleason score+ECOG status+patient group  Equation (8)

Example 4: Orthogonal Analyses of Data—Machine Learning Approaches

To evaluate gene expression profiles to determine overall survival (OS) in a subject with metastatic castration-resistant prostate cancer (mCRPC) after treatment with sipuleucel-T, techniques developed in the field of machine learning may be used. Machine learning was used to interrogate original qPCR validation and Affymetrix screening data. The approaches presented include LASSO (Lease Absolute Shrinkage and Selection Operator) and ElasticNet.

LASSO (Least Absolute Shrinkage and Selection Operator) is a statistical regression method known in the art which shrinks regression coefficients until some coefficients become zero. The assumption is feature sparsity in the dataset. The method penalizes based on least squares error and as the penalty increases, some coefficients become zero. A general reference to this statistical regression method can be found at Tibshirani, R. (1996), 'Regression Shrinkage and Selection via the Lasso', *Journal of the Royal Statistical Society* (Series B)58, 267-288, available at http://statweb.stanford.edu/~tibs/lasso/lasso.pdf.

ElasticNet is a methodology similar to LASSO in penalizing, and thereby reducing some regression coefficients to zero. The ElasticNet differs, however, in considering grouping effect. If some variables behave similarly, Lasso would pick one from the group, whereas ElasticNet will consider all variables. A general reference to the ElasticNet methodology can be found at Zou, H. & Hastie, T. (2003), 'Regularization and Variable Selection via the Elastic Net', *Journal of the Royal Statistical Society: Series* 8 (*Statistical Methodology*)67 (2), 301-320, available at https://web.stanford.edu/~hastie/Papers/B67.2%20(2005)%20301-320%20Zou %20&%20Hastie.pdf.

The LASSO and ElasticNet were applied to Affymetrix screening data. Eight genes were identified by LASSO and ElasticNet, wherein the first seven overlap between LASSO and ElasticNet: COL1A1, LAX1, DPPA4, CDK5RAP2, KCNQ5, ZFYVE28, DNAH11, and TAP2. The p-values of each gene is provided in Table 6 below.

TABLE 6

P value significance for association of Affymetrix candidate genes with survival

| Affymetrix probe | Gene Symbol | Sipuleucel-T subjects | Placebo subjects | All subjects |
| --- | --- | --- | --- | --- |
| '1556499_s_at' | COL1A1 | 0.0001 | 0.01 | 0.7158 |
| '207734_at' | LAX1 | 0.1263 | 0.0481 | 0.6815 |
| '232985_s_at' | DPPA4 | 0.2412 | 0.1432 | 0.5854 |
| '233540_s_at' | CDK5RAP2 | 0.0123 | 0.8928 | 0.1407 |
| '244623_at' | KCNQ5 | 0.0541 | 0.3482 | 0.1121 |
| '232408_at' | ZFYVE28 | 0.2467 | 0.6961 | 0.2733 |
| '204769_s_at' | TAP2 | 0.1356 | 0.4816 | 0.9606 |
| '1553159_at' | DNAH11 | 0.02 | 0.7439 | 0.477 |
| '1556499_s_at' | COL1A1 | 0.0001 | 0.01 | 0.7158 |

This gene data can be combined to derive a composite score that can be very strongly predictive of overall survival after treatment with sipuleucel-T. It was found that upregulation of LAX1, DPPA4, KCNQ5, and ZFYVE28 and down regulation of COL1A1, CDK5RAP2, and TAP2 is associated with better overall survival. A composite gene expression score was created by linearly combining the log expressions of the genes, keeping in consideration the direction of association:

Composite Expression: −Log expression (COL1A1)+ Log expression (LAX1)+Log expression (DPPA4)−Log expression (CDK5RAP2)+Log expression (KCNQ5)+Log expression (ZFYVE28)+Log expression (DNAH11)−Log expression (TAP2)  Equation (14)

The above composite expression was very strongly associated with overall survival in IMPACT. As shown in FIG. 7, the Kaplan-Meier method was used to show survival of the patient groups described above. The plot shows that patients within the top tertile of composite expression score of equation (14) in the sipuleucel-T arm were more likely to survive relative to a control group. In fact, the top tertile expression have extremely strong relationship with (p<0.00001) overall survival.

According to the above results, the present application provides the combinations of biomarkers for predicting overall survival of a subject with mCRPC in response to treatment with sipuleucel-T.

According to the above, an embodiment of the present application includes administering sipuleucel-T to the subject based on the composite gene expression score that is higher or lower than an expression threshold that is relative to a control group of subjects that do not meet the expression threshold.

The invention claimed is:

1. A method of treating a patient having metastatic castration-resistant prostate cancer (mCRPC), the method comprising the steps of:
    (a) obtaining a biological sample from the patient, wherein the biological sample is selected from the group consisting of whole blood, peripheral blood mononuclear cells (PBMCs), circulating tumor cells (CTCs), and tumor tissue;
    (b) measuring in the biological sample an expression product level of at least two biomarkers selected from the group consisting of SYNGR3, AURKC, CHI3L2, SNTB1, ZNF268, COL1A1, LAX1, DPPA4, CDK5RAP2, KCNQ5, ZFYVE28, DNAH11, and TAP2;
    (c) determining a first composite score of expression product levels of the biomarkers measured in step (b), the first composite score corresponding to a probability of overall survival in response to treatment with sipuleucel-T; and
    (d) administering an immunotherapy sipuleucel-T to the patient based on the first composite score that is higher or lower than an expression threshold that is relative to a control group of subjects that do not meet the expression threshold.

2. The method of claim 1, wherein the biomarkers measured to determine the first composite score are selected from the group consisting of SNTB1, SYNGR3, AURKC, ZNF268, and CHI3L2.

3. The method of claim 1, wherein the biomarkers measured to determine the first composite score are selected from the group consisting of COL1A1, LAX1, DPPA4, CDK5RAP2, KCNQ5, ZFYVE28, DNAH11, and TAP2.

4. The method of claim 2, further comprising the step of steps of:
    correlating (i) the first composite score of the biomarker expression product levels of SNTB1, SYNGR3, AURKC, ZNF268, and CHI3L2 of the patient and (ii) the PSA level, LDH level, Alkaline phosphatase level, Hemoglobin level, Total Gleason Score, and ECOG status to reference values of (i) and (ii) from mCRPC patients grouped into overall survival groups; and
    classifying the patient into one of the overall survival groups based upon the patient's score relative to the reference values of (i) and (ii).

5. The method of claim 3, further comprising the step of steps of:
    correlating (i) the first composite score of the biomarker expression product levels of COL1A1, LAX1, DPPA4, CDK5RAP2, KCNQ5, ZFYVE28, DNAH11, and TAP2 of the patient and (ii) the PSA level, LDH level, Alkaline phosphatase level, Hemoglobin level, Total Gleason Score, and ECOG status to reference values of (i) and (ii) from mCRPC patients grouped into overall survival groups; and
    classifying the patient into one of the overall survival groups based upon the patient's score relative to the reference values of (i) and (ii).

6. The method of claim 2, wherein the first composite score uses a log expression of the biomarkers SNTB1, SYNGR3, AURKC, ZNF268, and CHI3L2 calculated as:

Log Expression (SNTB1)−Log Expression (SYNGR3)−Log Expression (AURKC)−Log Expression (ZNF268)+Log Expression (CHI3L2).

7. The method of claim 6, wherein a p-value of an association of an upregulation of biomarkers SNTB1 and CHI3L2 and a downregulation of biomarkers SYNGR3, AURKC, and ZNF268 to overall survival is less than 0.05.

8. The method of claim 3, wherein the first composite score uses a log expression of the biomarkers COL1A1, LAX1, DPPA4, CDK5RAP2, KCNQ5, ZFYVE28, DNAH11, and TAP2 calculated as:

−Log Expression (COL1A1)+Log Expression (LAX1)+Log Expression (DPPA4)+Log Expression (CDK5RAP2)+Log Expression (KCNQ5)+Log Expression (ZFYVE28)+Log Expression (DNAH11)−Log Expression (TAP2).

9. The method of claim 8, wherein a p-value of an association of an upregulation of biomarkers LAX1, DPPA4, KCNQ5, ZFYVE28, DNAH11 and a downregulation of biomarkers COL1A1, CDK5RAP2, and TAP2 to overall survival is less than 0.05.

10. A method of treating a patient having metastatic castration-resistant prostate cancer (mCRPC), the method comprising the steps of
    (a) obtaining a biological sample from the patient, wherein the biological sample is selected from the group consisting of whole blood, peripheral blood mononuclear cells (PBMCs), circulating tumor cells (CTCs), and tumor tissue;
    (b) using a kit for measuring in the biological sample an expression product level of at least one of the biomarkers selected from the group consisting of SYNGR3, AURKC, CHI3L2, SNTB1, ZNF268, COL1A1, LAX1, DPPA4, CDK5RAP2, KCNQ5, ZFYVE28, DNAH11, and TAP2, the kit comprising a plurality of oligonucleotide primers, wherein the plurality of primers consist essentially of at least one pair of oligonucleotide primers for amplification of at least one of the biomarkers selected from the group consisting of SYNGR3, AURKC, CHI3L2, SNTB1, ZNF268, COL1A1, LAX1, DPPA4, CDK5RAP2, KCNQ5, ZFYVE28, DNAH11, and TAP2, wherein the expression product is RNA or cDNA;
    (c) determining a first composite score of expression product levels of the biomarkers measured in step (b), the first composite score corresponding to a probability of overall survival in response to treatment with sipuleucel-T; and
    (d) administering an immunotherapy sipuleucel-T to the patient based on the first composite score that is higher or lower than an expression threshold that is relative to a control group of subjects that do not meet the expression threshold.

11. The method of claim 10, wherein the biomarker expression product levels measured are selected from the group consisting of SNTB1, SYNGR3, AURKC, ZNF268, and CHI3L2.

12. The method of claim 11, further comprising correlating the first composite score of the expression product levels of the biomarkers measured in step (b) to reference expression values from mCRPC patients grouped into overall survival groups, wherein the step of correlating the first composite score further comprises correlating (i) the first composite score of the biomarker expression product levels of SNTB1, SYNGR3, AURKC, ZNF268, and CHI3L2 of the patient and (ii) the PSA level, LDH level, Alkaline phosphatase level, Hemoglobin level, Total Gleason Score, ECOG status to reference values of (i) and (ii) from mCRPC patients grouped into overall survival groups.

13. The method of claim 12, wherein the first composite score of the expression levels of the biomarkers SNTB1, SYNGR3, AURKC, ZNF268, and CHI3L2 is calculated using the log expressions of SNTB1, SYNGR3, AURKC, ZNF268, and CHI3L2 as follows:

> Log Expression (SNTB1)−Log Expression (SYNGR3)−Log Expression (AURKC)−Log Expression (ZNF268)+Log Expression (CHI3L2).

14. The method of claim 10, wherein the biomarker expression product levels measured are selected from the group consisting of COL1A1, LAX1, DPPA4, CDK5RAP2, KCNQ5, ZFYVE28, DNAH11, and TAP2.

15. The method of claim 14, further comprising correlating the first composite score of the expression product levels of the biomarkers measured in step (b) to reference expression values from mCRPC patients grouped into overall survival groups, wherein the step of correlating the first composite score further comprises correlating (i) the first composite score of the biomarker expression product levels of COL1A1, LAX1, DPPA4, CDK5RAP2, KCNQ5, ZFYVE28, DNAH11, and TAP2 of the patient and (ii) the PSA level, LDH level, Alkaline phosphatase level, Hemoglobin level, Total Gleason Score, ECOG status to reference values of (i) and (ii) from mCRPC patients grouped into overall survival groups.

16. The method of claim 15, wherein the first composite score of the expression levels of the biomarkers COL1A1, LAX1, DPPA4, CDK5RAP2, KCNQ5, ZFYVE28, DNAH11, and TAP2 is calculated using the log expressions of COL1A1, LAX1, DPPA4, CDK5RAP2, KCNQ5, ZFYVE28, DNAH11, and TAP2 as follows:

> −Log Expression (COL1A1)+Log Expression (LAX1)+Log Expression (DPPA4)−Log Expression (CDK5RAP2)+Log Expression (KCNQ5)+Log expression (ZFYVE28)+Log expression (DNAH11)−Log expression (TAP2).

* * * * *